US007674752B2

(12) United States Patent
He et al.

(10) Patent No.: US 7,674,752 B2
(45) Date of Patent: Mar. 9, 2010

(54) FUNCTIONAL PROTEIN ARRAYS

(75) Inventors: Mingyue He, Cambridge (GB); Michael John Taussig, Cambridge (GB)

(73) Assignee: Discema Limited, Cambridge (GB)

( * ) Notice: Subject to any disclaimer, the term of this patent is extended or adjusted under 35 U.S.C. 154(b) by 600 days.

(21) Appl. No.: 10/344,607

(22) PCT Filed: Aug. 15, 2001

(86) PCT No.: PCT/GB01/03657

§ 371 (c)(1),
(2), (4) Date: May 13, 2003

(87) PCT Pub. No.: WO02/14860

PCT Pub. Date: Feb. 21, 2002

(65) Prior Publication Data

US 2004/0161748 A1    Aug. 19, 2004

(30) Foreign Application Priority Data

| Aug. 15, 2000 | (GB) | ................. | 0020016.2 |
| Dec. 1, 2000 | (GB) | ................. | 0029309.2 |
| Mar. 16, 2001 | (GB) | ................. | 0106610.9 |
| Jun. 7, 2001 | (GB) | ................. | 0113883.3 |
| Jul. 14, 2001 | (GB) | ................. | 0117232.9 |

(51) Int. Cl.
*C40B 50/06* (2006.01)
*C40B 40/04* (2006.01)
*A61K 38/00* (2006.01)
*C07K 2/00* (2006.01)
*C07K 5/00* (2006.01)
*C07K 14/00* (2006.01)
*C07K 17/00* (2006.01)

(52) U.S. Cl. ...................... 506/26; 506/15; 530/300; 530/350

(58) Field of Classification Search .................... 506/26, 506/15; 530/300, 350
See application file for complete search history.

(56) References Cited

U.S. PATENT DOCUMENTS 5,843,701 A * 12/1998 Gold et al. ............... 435/68.1
6,800,453 B2 10/2004 Labaer et al. ............. 435/68.1

FOREIGN PATENT DOCUMENTS

| EP | 0818467 | 1/1998 |
| WO | WO98/31700 | 7/1998 |
| WO | WO99/35289 | 7/1999 |
| WO | WO00/04382 | 1/2000 |
| WO | WO00/32823 | 6/2000 |
| WO | WO01/51663 | 7/2001 |

OTHER PUBLICATIONS

Nicholls et al. Journal of Immunological Methods; vol. 165: 81-91; 1993.*
Hanes et al. FEBS Letters. vol. 450 (1-2): 105-110; Apr. 30, 1999.*
Mori et al. Endocrinologia Japonica. Apr. 1985; vol. 32(2):271-278; Abstract only.*
Tenson et al. Cell. vol. 108: 591-594. Mar. 8, 2002.*
Afanassiev et al., Nucleic Acids Research 28(12): i-iv (2000).
Büssow et al., Genomics 65: 1-8 (2000).
Büssow et al., Nucleic Acids Research 26(21): 5007-5008 (1998).
Emili et al., Nature Biotechnology 18: 393-397 (2000).
Ge, Nucleic Acids Research 28(2): i-vii (2000).
Geysen et al., Proc. Natl. Acad. Sci. USA 81: 3998-4002 (1984).
He et al., Nucleic Acids Research 29(15): 106 (2001).
Hoffmüller et al., Angew. Chem. Int. Ed. 37(23): 3241-3243 (1998).
Holt et al., Nucleic Acids Research 28(15): i-v (2000).
Lueking et al., Analytical Biochemistry 270: 103-111 (1999).
Martzen et al., Science 286: 1153-1155 (1999).
Ohuchi et al., Nucleic Acids Research 26(19): 4339-4346 (1998).
Pandey et al., Nature 405: 837-846 (2000).
Robinson et al., Proc. Natl. Acad. Sci. USA 95: 5929-5934 (1998).
Uetz et al., Nature 403: 623-627 (2000).
Walter et al., Current Opinion in Microbiology 3: 298-302 (2000).
Ye et al., Proc. Natl. Acad. Sci. USA 91: 12629-12633 (1994).
Angenendt et al., Molecular & Cellular Proteomics 5: 1658-1666 (2006).
Bernabeu et al., Proc. Natl. Acad. Sci. USA 79: 3111-3115 (1982).
Hanes et al., Proc. Natl. Acad. Sci. USA 94: 4937-4942 (1997).
Hardesty et al., Progress in Nucleic Acid Research and Molecular Biology 66: 41-66 (2001).
He et al., Current Opinion in Biotechnology 18: 1-6 (2007).
He et al., Nucleic Acids Research 25(24): 513205134 (1997).
Komar et al., The Journal of Biological Chemistry 272(16): 10646-10651 (1997).
Mattheakis et al., Proc. Natl. Acad. Sci. USA 91: 9022-9026 (1994).
Palmer et al., Protein Science 15: 2842-2846 (2006).
Ramachandran et al., Science 305: 86-90 (2004).
Voss et al., J. Mol. Biol. 360: 893-906 (2006).
Hsu et al., PNAS 104(42): 16516-16521 (2007).
Haab et al., Genome Biology 1(6): 1-22 (2000).
MacBeath et al., Science 289: 1760-1763 (2000).
Schweitzer et al., Proteomics 3: 2190-2199 (2003).
Wilson et al., Current Opinion in Chemical Biology 6:81-85 (2001).
Zhu et al., Science 293: 21012105 (2001).
Zhu et al., Current Opinion in Chemical Biology 5: 40-45 (2001).

* cited by examiner

*Primary Examiner*—Sue Liu
(74) *Attorney, Agent, or Firm*—Perkins Coie LLP

(57) ABSTRACT

The present invention relates to a method for producing a protein array starting from DNA (or mRNA) in which a number of native, functional proteins, domains or peptides are produced in parallel by in in vitro synthesis using a cell free system for transcription and translation. The products are immobilised in a gridded format on a surface, using an isolation sequence tag incorporated into the proteins.

12 Claims, 20 Drawing Sheets

Figure 5:
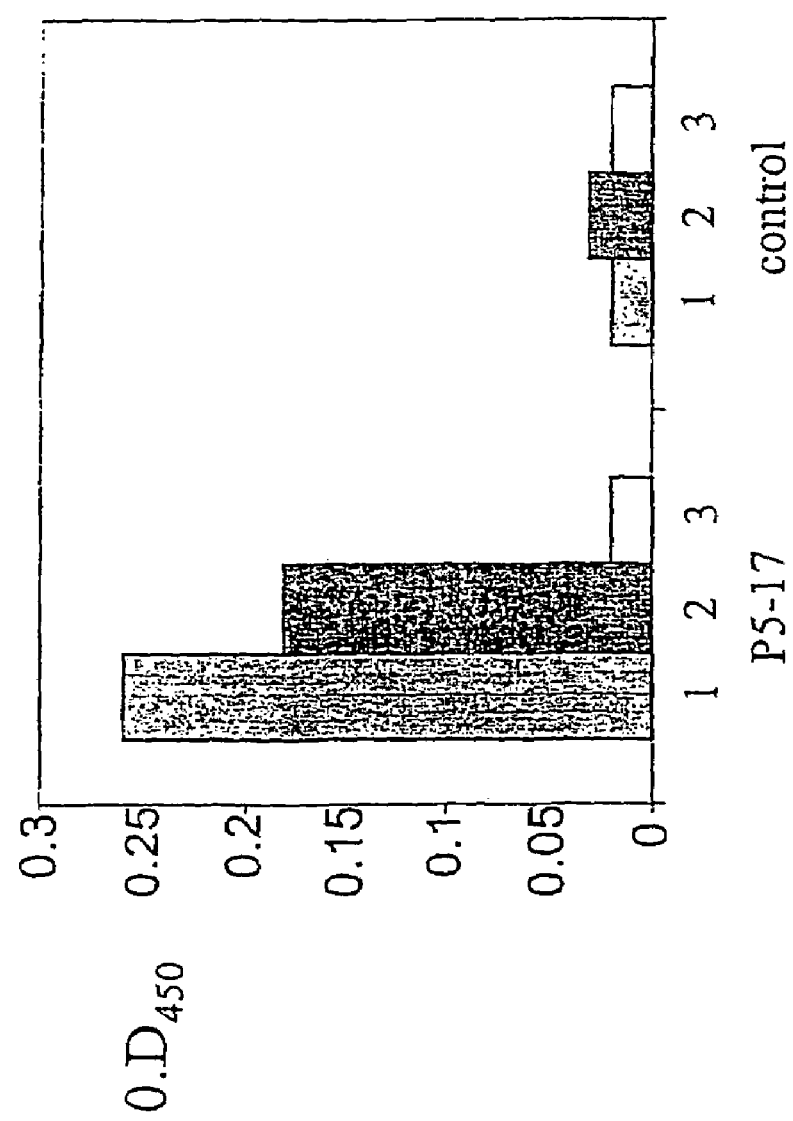

Figure 1
*Construct with downstream (C-terminal) tag*
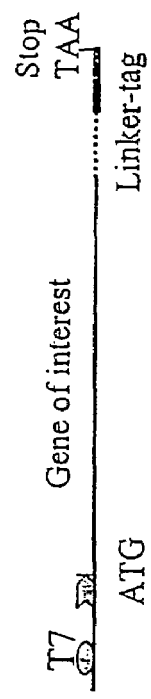
*Construct with upstream (N-terminal) tag*
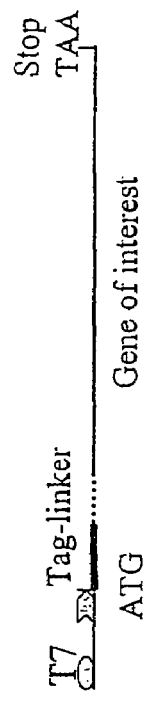
T7: T7 promoter; ⇨ Protein expression signal; ATG: start codon
▬ : tag sequence; ...... : peptide linker

Figure 2(a) [SEQ ID No. 11]

T7 promoter
5'-GCA GCT AAT *ACG ACT CAC TAT AGG* AAC AGA *CCACC* ATG-3'
                                                     Kozak

Figure 2(b) [SEQ ID No. 12]

T7 promoter
5'-GCA GCT *AAT ACG ACT CAC TAT AGG* GA <u>GAAGGAGA</u>*CCACC* ATG-3'
                                        S/D        Kozak

Figure 3 a. (Single hexahistidine) – linker upstream: *CAT CAC CAT CAC CAT CAC GGC GGT GGC TCT GGT GGC GGT TCT GGC GGT GGC ACC GGT GGC GGT TCT GGC GGT GGC* [SEQ ID No. 13],
encoding HHHHHHGGGSGGGSGGGTGGGSGGG [SEQ ID No. 14].

b. (Double hexahistidine) – linker upstream: *CAT CAC CAT CAC CAT CAC TCT AGA GCT TGG CGT CAC CCG CAG TTC GGT GGT CAC CAC CAC CAC CAC CAC GGC GGT GGC TCT GGT GGC GGT TCT GGC GGT GGC ACC GGT GGC GGT TCT GGC GGT GGC* [SEQ ID No. 15],
encoding HHHHHHSRAWRHPQFGGHHHHHHGGGSGGGSGGGTGGGSGGG [SEQ ID No. 16].

c. (Single hexahistidine) – linker downstream: *GGC GGT GGC TCT GGT GGC GGT TCT GGC GGT GGC ACC GGT GGC GGT TCT GGC GGT GGC CAT CAC CAT CAC CAT CAC* [SEQ ID No. 17],
encoding GGGSGGGSGGGTGGGSGGGHHHHHH [SEQ ID No. 18].

d. (Double hexahistidine) – linker downstream: *GGC GGT GGC TCT GGT GGC GGT TCT GGC GGT GGC ACC GGT GGC GGT TCT GGC GGT GGC CAT CAC CAT CAC CAT CAC TCT AGA GCT TGG CGT CAC CCG CAG TTC GGT GGT CAC CAC CAC CAC CAC CAC* [SEQ ID No. 19],
encoding GGGSGGGSGGGTGGGSGGGHHHHHHSRAWRHPQFGGHHHHHH [SEQ ID No. 20].

Figure 4
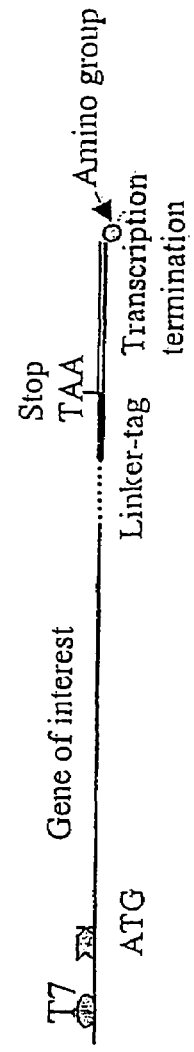
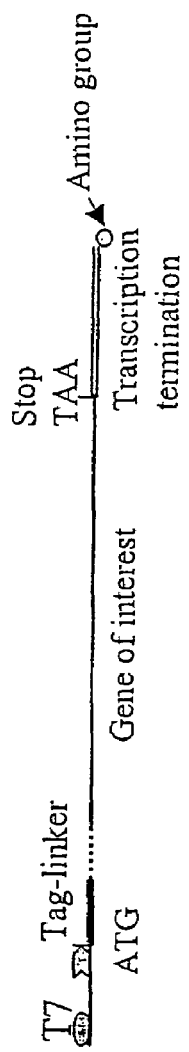

```
                          SEQUENCE LISTING

<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His polypeptide

<400> SEQUENCE: 1

His His His His His His
 1               5

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His His His His His His Ser Arg Ala Trp Arg His Pro Gln Phe Gly
 1               5                  10                  15

Gly His His His His His His
             20

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 taataa                                                             6

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: PCR Primer

<400> SEQUENCE: 4
gcagctaata cgactcacta taggaacaga ccaccatgsa ggtscasctc gagsagtctg    60
g                                                                   61

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 5
gccaccgcct ctagagcggc tcagcgtcag ggtgctgct                          39

<210> SEQ ID NO 6
<211> LENGTH: 83
<212> TYPE: DNA
<213> ORGANISM: Artificial Sequence
```

```
<220> FEATURE:
<223> OTHER INFORMATION: Description of Artificial Sequence: PCR Primer

<400> SEQUENCE: 6
gctctagagg cggtggctct ggtggcggtt ctggcggtgg caccggtggc ggttctggcg      60
gtggcaaacg ggctgatgct gca                                              83

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 7
tccggatata gttcctcc                                                    18

<210> SEQ ID NO 8
<211> LENGTH: 272
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctctagagg cggtggctct ggtggcggtt ctggcggtgg caccggtggc ggttctggcg      60
gtggcaaacg ggctgatgct gcacatcacc atcaccatca ctctagagct tggcgtcacc    120
cgcagttcgg tggtcaccac caccaccacc actaataaaa aaaaaaaaaa aaaaaaaaa    180 aaaaaaccgc tgagcaataa ctagcataac cccttggggc ctctaaacgg gtcttgaggg    240
gttttttgct gaaaggagga actatatccg ga                                   272

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcagctaata cgactcacta taggaacaga ccaccatgga agacgccaaa aac            53

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gccaccgcct ctagagcgca atttggactt tccgcc                                36

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```

-continued gcagctaata cgactcacta taggaacaga ccaccatg                                    38

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcagctaata cgactcacta tagggagaag gagaccacca tg                               42

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catcaccatc accatcacgg cggtggctct ggtggcggtt ctggcggtgg caccggtggc            60
ggttctggcg gtggc                                                            75

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 14

His His His His His His Gly Gly Gly Ser Gly Gly Gly Ser Gly Gly
 1               5                  10                  15

Gly Thr Gly Gly Gly Ser Gly Gly Gly
            20                  25

<210> SEQ ID NO 15
<211> LENGTH: 126
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
catcaccatc accatcactc tagagcttgg cgtcacccgc agttcggtgg tcaccaccac            60
caccaccacg gcggtggctc tggtggcggt tctggcggtg gcaccggtgg cggttctggc           120
ggtggc                                                                     126

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 16

His His His His His His Ser Arg Ala Trp Arg His Pro Gln Phe Gly
 1               5                  10                  15

Gly His His His His His His Gly Gly Gly Ser Gly Gly Gly Ser Gly

Gly Gly Thr Gly Gly Gly Ser Gly Gly Gly
            35                  40

<210> SEQ ID NO 17
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcggtggct ctggtggcgg ttctggcggt ggcaccggtg gcggttctgg cggtggccat    60
caccatcacc atcac                                                    75

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 18

Gly Gly Gly Ser Gly Gly Gly Ser Gly Gly Gly Thr Gly Gly Gly Ser
  1               5                  10                  15

Gly Gly Gly His His His His His His
            20                  25

<210> SEQ ID NO 19
<211> LENGTH: 126
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcggtggct ctggtggcgg ttctggcggt ggcaccggtg gcggttctgg cggtggccat    60
caccatcacc atcactctag agcttggcgt acccgcagt tcggtggtca ccaccaccac   120
caccac                                                             126

<210> SEQ ID NO 20
<211> LENGTH: 42
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 20

Gly Gly Gly Ser Gly Gly Gly Ser Gly Gly Gly Thr Gly Gly Gly Ser
  1               5                  10                  15

Gly Gly Gly His His His His His His Ser Arg Ala Trp Arg His Pro
            20                  25                  30

Gln Phe Gly Gly His His His His His His
            35                  40

FUNCTIONAL PROTEIN ARRAYS

This application is a 371 of PCT/GB01/03657 on Aug. 15, 2001, which is hereby incorporated by reference.

BACKGROUND

An array is a precisely ordered arrangement of elements, allowing them to be displayed and examined in parallel (1). It usually comprises a set of individual species of molecules or particles arranged in a regular grid format; the array can be used to detect interactions, based on recognition or selection, with a second set of molecules or particles applied to it. Arrays possess advantages for the handling and investigation of multiple samples. They provide a fixed location for each element such that those scoring positive in an assay are immediately identified; they have the capacity to be comprehensive and of high density, they can be made and screened by high throughput robotic procedures using small volumes of reagents; and they allow the comparison of each assay value with the results of many identical assays. The array format is well established for global analysis of nucleic acids, and oligonucleotide and cDNA arrays (DNA chips) are used for gene expression analysis. In a familiar format, large numbers (e.g. thousands) of DNA hybridisation probes are attached in an ordered pattern to a surface such as nylon, glass or silicon and hybridised to fluorescently labelled whole cell mRNA or cDNA, the quantitative signals on each array element are measured in parallel by means of a reader device.

The array approach may also be adapted for display of peptides and proteins; the elements displayed may be a set of related proteins or peptides, or the entire protein complement of an organism. Protein array technology allows high throughput screening for gene expression and molecular interactions. It is possible to use protein arrays to examine in parallel the functions of thousands of proteins previously known only by their DNA sequence. For functional information to be obtained, the arrayed proteins must be in native form. However, some preparative methods cause protein denaturation, as may occur during extraction or release of recombinant proteins from bacteria, and the use of arrays from such starting material is therefore limited to applications determined only by the primary sequence of the protein rather than tertiary structure. In order to develop high throughput approaches to global protein analysis which can yield functional information, methods for producing arrays in which proteins retain their functions are required.

Arrays of immobilised proteins can be used to demonstrate a binding reaction, as where the array is exposed to an entity such as an antibody or ligand, which may be directly or indirectly labelled, and binding demonstrated by localisation of the label to a particular segment of the array. Mass spectrometry may also be used to identify binding interactions on the array. Alternatively, the arrayed proteins may be in solution and used to study biochemical function. Potential uses of protein arrays which have been discussed in the literature (1-12) include identification of antibodies and analysis of antibody specificity, measurement of global protein expression, identification of ligand-receptor interactions and protein-protein interactions, and screening and selecting proteins or ligands from libraries. (i) Expression profiling. One type of protein array which has been proposed is based on immobilisation of antibodies at a surface (an antibody array). In principle, the reaction of an antibody array with cellular proteins can provide a global quantitative readout of all the proteins expressed at any particular time (proteome analysis). In one version, for differential display, the array is probed with fluorescently labelled proteins from two different cell states; cell lysates are labelled by different fluorophores and mixed such that the colour acts as a readout for the change in abundance. (ii) Antibody detection. A second application is the detection of antibodies against cellular proteins, where either or both partners are unknown. Thus an array of cellular proteins can be used to select antibodies from libraries of soluble antibodies or from phage-display or ribosome-display libraries. The antigen array can also be used to analyse antibodies in small amounts of patient sera, as during infections or in autoimmune conditions. (iii) Ligand screening. An array of potential target proteins, such as receptors, can be used as a screen for selection of ligands which may be possible drug candidates, including small molecules, peptides, aptamers, nucleic acids or synthetic scaffolds. (iv) Detection of protein-protein interactions A further use for protein arrays is in the detection of protein-protein interactions. Each protein in the genome may interact with a number of partners, so for the approximately 100,000 proteins encoded in the human genome there may exist millions of interactions. Such interactions are often measured by yeast two-hybrid (cell-based) methods but these may fail to measure interactions involving secreted proteins, proteins with disulphide bridges and membrane bound proteins such as receptors. An array method would be highly desirable in these cases and may reveal interactions which are not detected by the cellular methods.

Literature Descriptions of Preparation of Protein Arrays

The arrays described to date are composed either of purified proteins or proteins expressed in living cells or viruses. Early examples were peptide arrays, in which peptides were chemically synthesised on a solid support and used to identify epitopes recognised by antibodies (2). Peptide arrays can be chemically synthesised up to a length of about 30 amino acids, but are unable to produce full length folded proteins.

Clearly, protein arrays can be made by chemical or noncovalent attachment of preformed proteins onto suitable surfaces, such as treated glass slides or absorptive membranes such as nitrocellulose or PVDF. For high throughput studies, such as proteomics or library screening, this requires methods for the preparation, purification and immobilisation in parallel of large numbers of proteins. Methods for production of recombinant proteins from bacteria for assay in an arrayed format have been described (3,6-10). Proteins can be expressed as constructs fused to an affinity tag (e.g. hexahistidine) or glutathione S-transferase (GST), recovered by cell lysis and used either as crude lysates or after affinity purification (e.g. on Ni-NTA metal affinity columns). However, the production of recombinant proteins in bacterial systems can be problematic due to aggregation, insoluble inclusion bodies and/or degradation of the product, while eukaryotic systems suffer from lower yields and high demands on sterility or time consuming cloning procedures (e.g. Baculovirus). Where denaturants are used in the extraction the protein will often be rendered nonfunctional. Once the proteins have been isolated, various technical formats, substrates, production methods and detection systems are available (reviewed in 8).

Martzen et al. (3) purified most of the soluble yeast proteins from *Saccharomyces cerevisiae* by glutathione agarose affinity chromatography from 6144 yeast strains each of which contained a plasmid with a different yeast ORF (open reading frame) fused to GST. Proteins were assayed in solution for a particular enzymatic activity. Since the proteins were purified in native form, this constituted a functional protein array, although the proteins were not immobilised on a surface. Yeast cells have been used to create a 'living' recombinant protein array, containing about 6000 colonies, each of which expresses a different ORF Gal4-fusion protein (4). This is basically a cellular, yeast two hybrid screen performed in a 96 well plate format.

Arrays can be prepared by inducing the simultaneous expression of large numbers of cDNA clones in an appropriate vector system and high speed arraying of protein products. Bussow et al. (6) arrayed proteins expressed from cDNA clones of a human fetal brain cDNA expression library hEx1 cloned in *Escherichia coli*. The his6 (hexahistidine)-tagged proteins were induced from individual colonies grown in 384well microtiter plates and gridded onto high density PVDF filter membranes prior to expression induction with IPTG. Release of the proteins from the bacterial cytoplasm created an array of proteins immobilised on the filters. Two example proteins were identified on the filters using antibodies. While this method allows the operator to screen expression libraries, the extraction procedure used 0.5M NaOH, during which process proteins were denatured and therefore rendered nonfunctional. In another report (below), proteins were extracted and solubilised using 6M guanidinium HCl, which is also a denaturant. Other drawbacks of this procedure as a means of producing an array are that clones must be extensively screened for in frame expression and that cDNA libraries contain many clones which lack the 5' end (N-terminal), may have multiple copies of some genes and poor representation of others.

Lueking et al. (9) gridded purified protein solutions from the hEx1 library onto PVDF filters, in an extension of classical dot-blotting methodology. For high throughput, small-scale protein expression, clones of the hEx1 library were grown in 96-well microtiter plates and induced with IPTG; cells were lysed with 6M guanidinium HCl and supernatants filtered through a 96 well filter plate onto a PVDF membrane. For larger scale production of purified proteins, peptide- and his6-tagged proteins were expressed from *E. coli* and isolated with Ni-NTA agarose. Results of high throughput screening showed quite a number of false positives, i.e. proteins detected by anti-tag which were in fact out of frame with the tag, and antibody specificity screening often showed unexpected crossreactions, mostly with ribosomal proteins, for no apparent reason. The use of guanidinium HCl denatures the proteins and may cause aberrant results.

Holt et al. (7) screened the hEx1 library to identity specific antibodies, reactive with denatured proteins, using 12 well-expressed antibody fragments of previously unknown specificity. Four specific interactions were identified In another example of dot blotting, Ge described an array system for detection of protein interactions with other proteins, DNA, RNA and small ligands (12). In this case, 48 highly purified, native proteins were arrayed on a nitrocellulose membrane, by spotting using a 96-well dot blot apparatus. The proteins were overexpressed in bacteria or baculovirus and purified to homogeneity. The dot blot array was reacted with a number of different radiolabelled probes (protein, DNA, RNA, ligand), followed by autoradiography and densitometry, and showed to behave in a functional manner, i.e. probes interacted with partner molecules with the expected specificity.

Afanassiev et al. (5) describe a method for making protein arrays using chemical coupling of proteins to an agarose film on microscope slides; the agarose is activated by sodium periodate to reveal aldehyde groups which bind amino groups on the protein. Varying amounts of an antigen (BAD) or an anti-BAD antibody (6A11) were immobilised and binding of the partner molecule detected by a fluorescent second reagent.

REFERENCES

1. Emili A. Q. and Cagney G. (2000) Large-scale functional analysis using peptide or protein arrays. Nature Biotechnology 18:393-397.
2. Geysen H. M., Meloen, R. H. and Barteling S. J. (1984) Use of peptide synthesis to probe viral antigens for epitopes to a resolution of a single amino acid. Proc. Natl Acad. Sci. USA 81:3998-4002.
3. Martzen M. R., McCraith S. M., Spinelli S. L., Torres F. M., Fields S., Grayhack E. J. and Phizicky E. M. (1992) A biochemical genomics approach for identifying genes by the activity of their products. Science November 5; 286 (5442): 1153-5.
4. Uetz P. et al. (2000) A comprehensive analysis of protein-protein interactions in *Saccharomyces cerevisiae*. Nature 403, 623-627.
5. Afanassiev V., Hanemann V. and Wolfl, S. (2000) Preparation of DNA and protein microarrays on glass slides coated with an agarose film. Nucleic Acids Research 28:E66.
6. Bussow K., Cahill D., et al. (1998) A method for global protein expression and antibody screening on high-density filters of an arrayed cDNA library. Nucleic Acids Res. 26:5007-5008.
7. Holt L. J., Bussow K, Walter G and Tomlinson I. M. (2000) By-passing selection: direct screening for antibody-antigen interactions using protein arrays. Nucleic Acids Research 28:e72.
8. Walter G., Bussow K., Cahill D., Lueking A. and Lehrach H. (2000) Protein arrays for gene expression and molecular interaction screening. Current Opinion in Microbiology 3:298-302.
9. Lueking A., Horn, M., Eickhoff, H., Bussow, K, Lehrach H. And Walter G. (1999) Protein Microarrays for gene Expression and Antibody Screening. Anal. Biochem. 270: 103-111.
10. Bussow K., Nordhoff E., Lubbert C., Lehrach H and Walter G. (2000) A human cDNA library for high-throughput protein expression screening. Genomics 65:1-8.
11. Pandey A. and Mann M. (2000) Proteomics to study genes and genomes. Nature 405:837-846.
12. Ge H. (2000) UPA, a universal protein array system for quantitative detection of protein-protein, protein-DNA, protein-RNA and protein-ligand interactions. Nucleic Acids Research 28, e3.

FIGURE LEGENDS

FIG. 1: Diagram of DNA constructs for in vitro expression and protein immobilisation.

FIG. 2(*a*): Upstream sequence elements [SEQ ID No. 11] for eukaryotic expression, showing T7 promoter (italics), and Kozak (italics) sequences.

FIG. 2(*b*): Upstream sequence elements [SEQ ID No. 12] for both prokaryotic and eukaryotic expression, showing T7 promoter (italics), Shine Delgarno (S/D) sequence (underlined) and Kozak (italics) sequences.

FIG. 3: DNA and protein sequences of hexahistidine and flexible linker.
[SEQ ID Nos: FIG. 3*a*=SEQ ID Nos. 13 (DNA) and 14 (protein)
FIG. 3*b*=SEQ ID Nos. 15 (DNA) and 16 (protein)
FIG. 3*c*=SEQ ID Nos. 17 (DNA) and 18 (protein)
FIG. 3*d*=SEQ ID Nos. 19 (DNA) and 20 (protein).]
FIG. 4: Diagram of DNA constructs for immobilisation prior to in vitro expression.

FIG. 5: Construction of a functional protein array element in situ after transcription and translation of DNA in vitro The P5-17 protein or control protein were synthesised from PCR DNA in vitro in 3 duplicated wells each and immobilised in situ via a double hexahistidine tag to Ni-NTA surface of HisSorb wells.

1. Binding of biotin-labelled progesterone-BSA, followed by HRP-streptavidin detection.
2. Binding of HRP-anti-human-κ antibodies.
3. Binding of HRP-streptavidin FIG. 6: Construction of a functional protein array element by transfer of protein to a secondary surface after transcription and translation of DNA in vitro The P5-17 protein or control proteins with double hexahistidine tags were synthesised from PCR DNA in vitro in non-coated polystyrene wells and transferred to HisSorb wells coated with Ni-NTA. Specific binding was detected with biotinylated progesterone-bovine serum albumin (*P-BSA), biotinylated BSA (*BSA), or biotinylated carcinembryonic antigen (*CEA) followed by HRP-streptavidin detection. Protein expression was detected with HRP-anti-human-κ antibodies.

Figure 7:
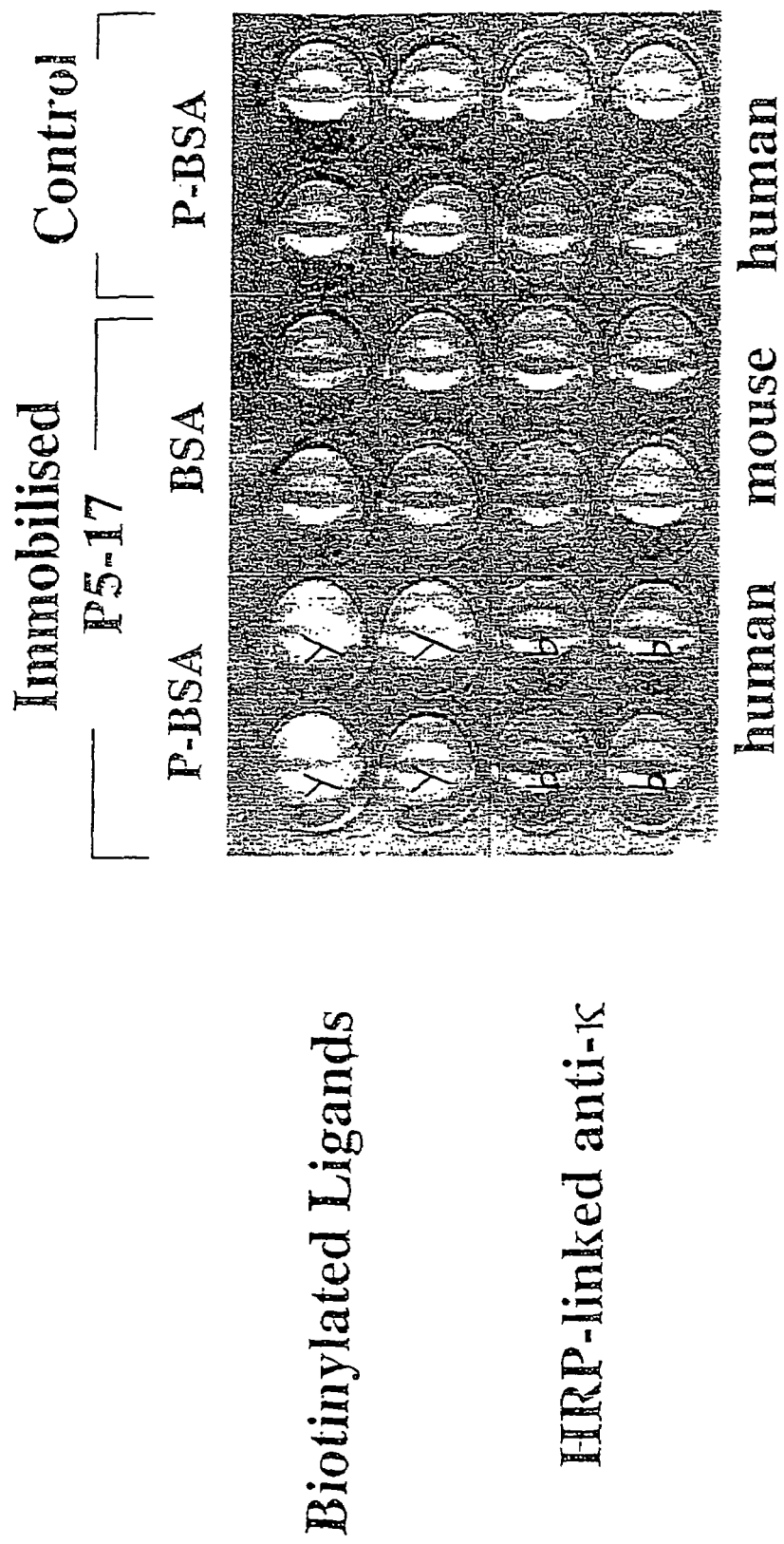

FIG. 7: Protein in situ array (PISA) of human single chain anti-progesterone $V_H$/K (P5-17). (For explanation see Results, Example 4): y=yellow colour; b=blue colour.

Figure 8:
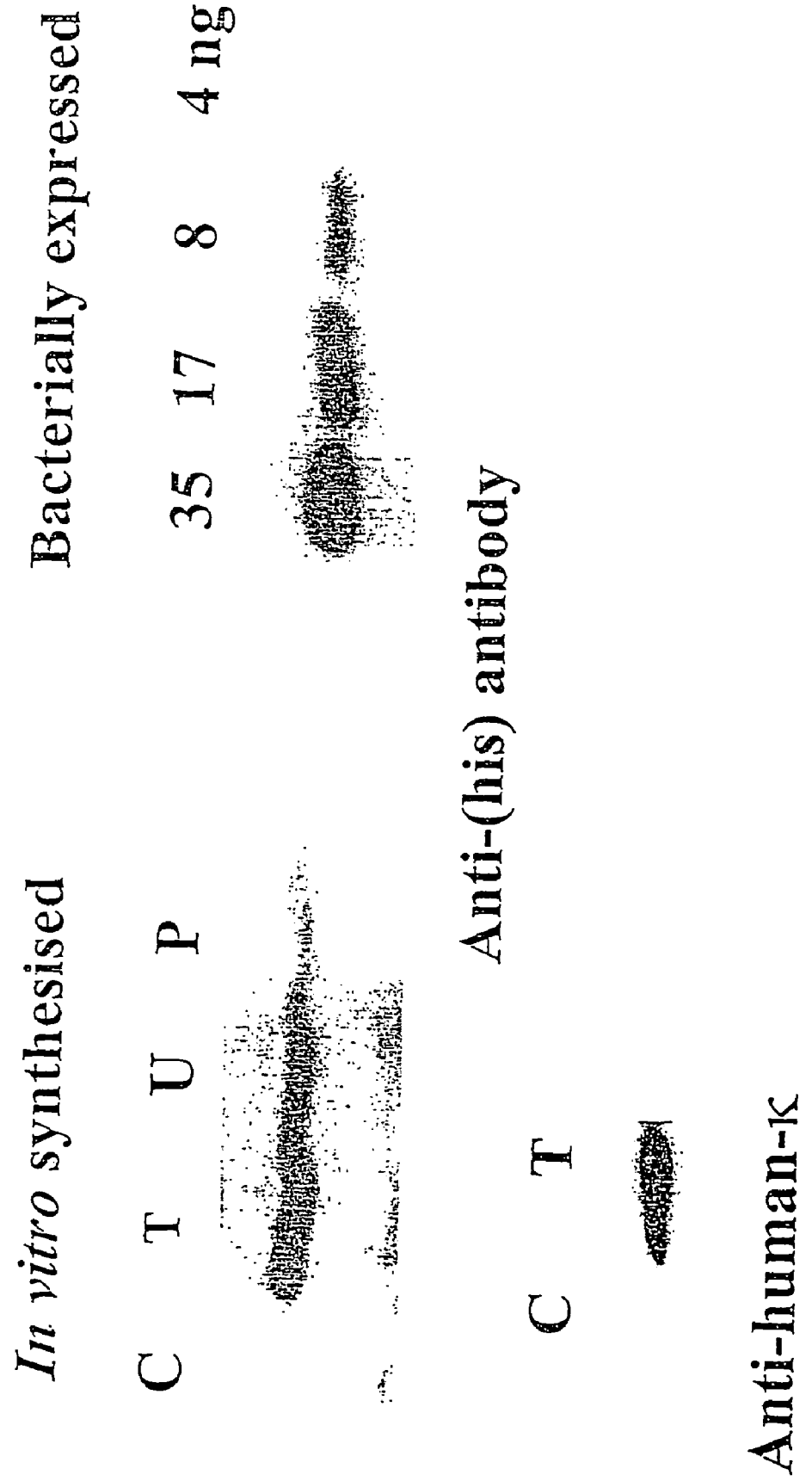

FIG. 8: Protein in situ array (PISA): Western blot quantitation of expression and immobilization of human $V_H$/K antibody fragment. Key: C=TNT Control, T=Total, U=Unbound fraction; P=PISA bound fraction (eluted).

Figure 9:
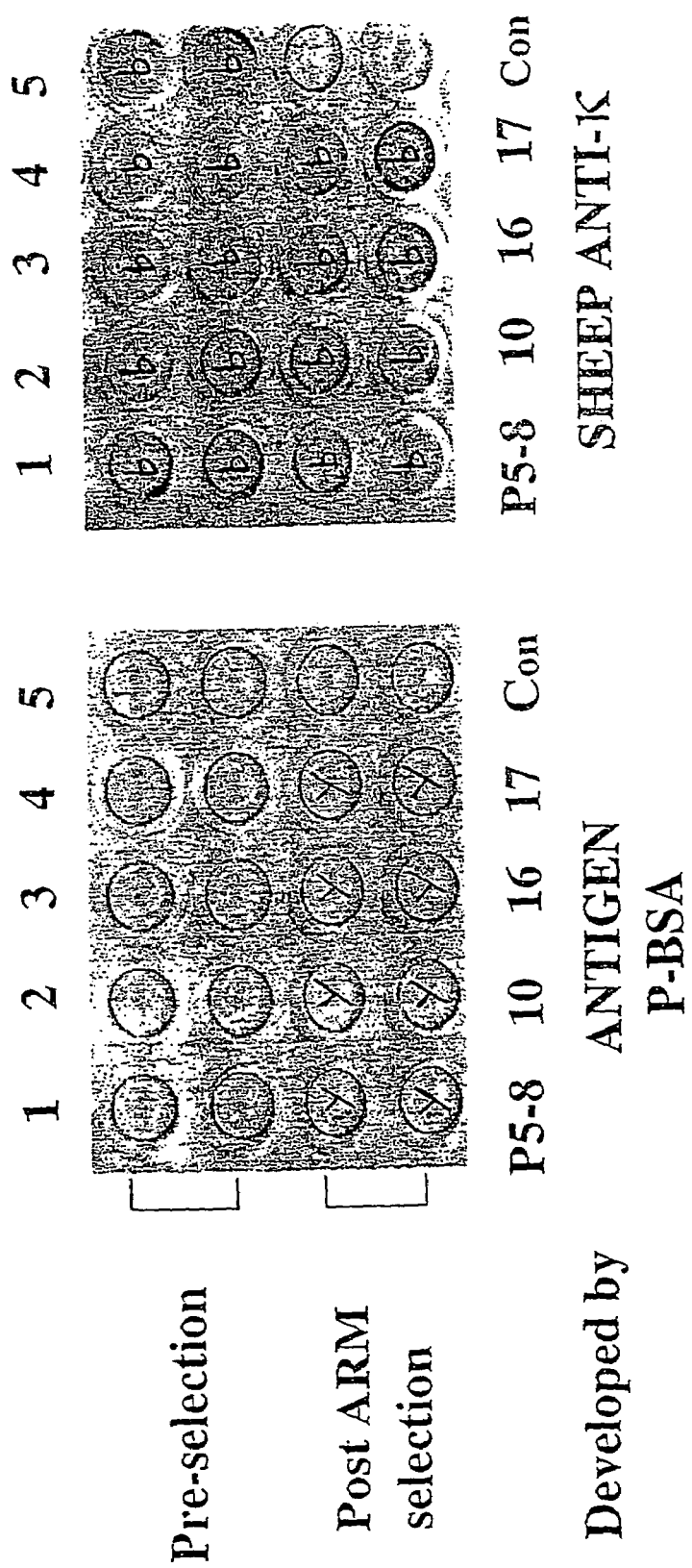

FIG. 9: Protein in situ array (PISA) arrays of cloned human $V_H$/K fragments from a transgenic library before and after selection in ARM display: y=yellow colour; b=blue colour.

Figure 10:
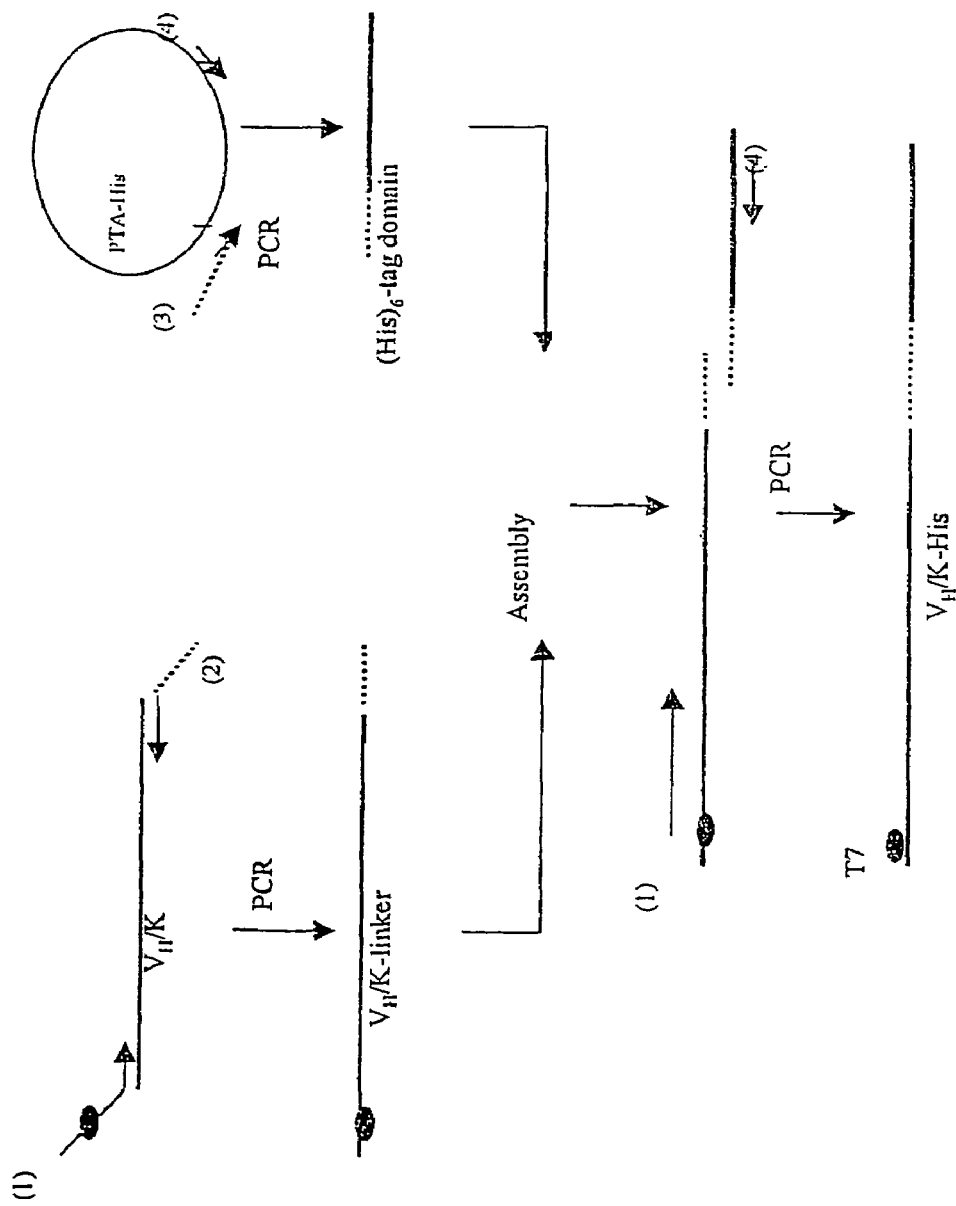

FIG. 10: Illustration of construction of DNA suitable for in vitro protein synthesis for PISA, using single chain antibody $V_H$/K fragments as example.

Figure 11:
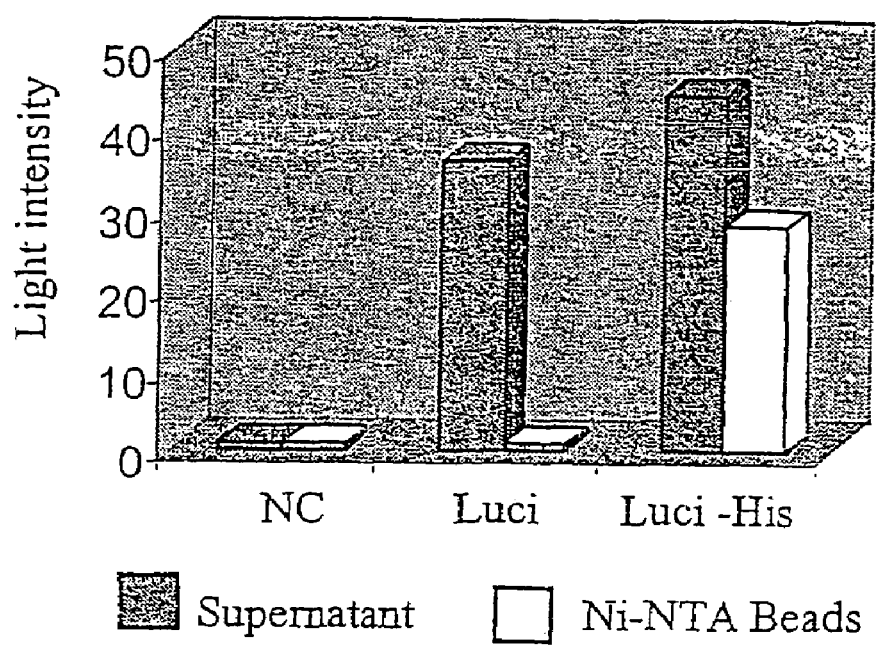

FIG. 11: Functional assay of free and PISA-immobilised luciferase by luminometry. Supernatant: TNT mixture after incubation with Ni-NTA magnetic agarose beads. NC: TNT mixture control lacking PCR DNA. Luci: TNT mixture containing the PCR construct encoding luciferase without double-His tag domain. Luci-His: TNT mixture containing the PCR construct encoding luciferase fused with double-His tag domain.

Figure 12:
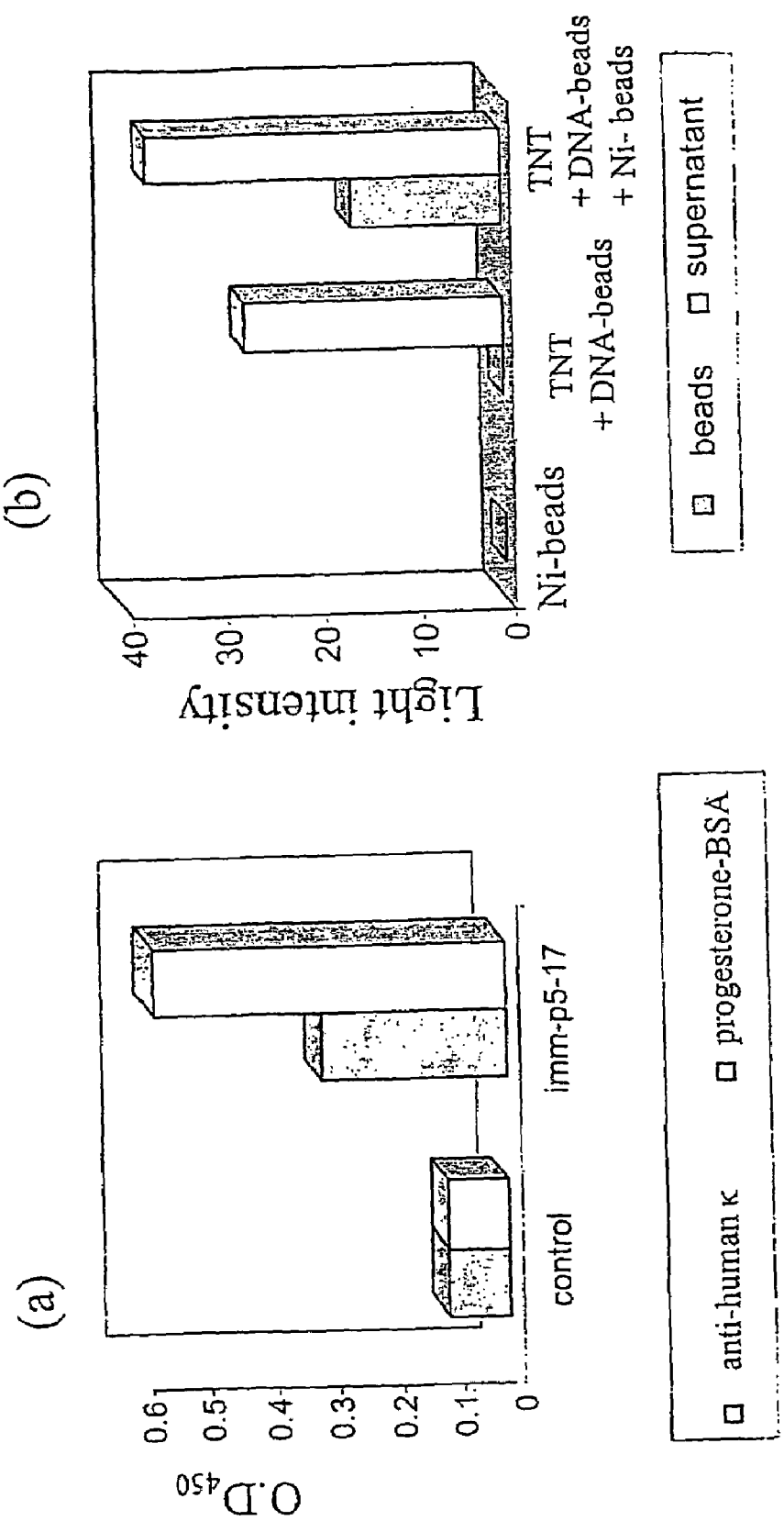

FIG. 12: Generation of protein array elements using immobilised PCR DNA.

P5-17 human anti-progesterone $V_H$/K fragment was immobilised on a Ni-NTA coated well (imm P5-17) after TNT cell free synthesis from P5-17 DNA-coupled beads. Control: DNA-coupled beads omitted.

Luciferase was immobilised on Ni-NTA beads after TNT cell free synthesis from luciferase DNA-coupled beads (TNT+DNA-beads+Ni-beads). Controls: Ni-NTA beads alone; TNT+DNA-coupled beads only.

Figure 13:
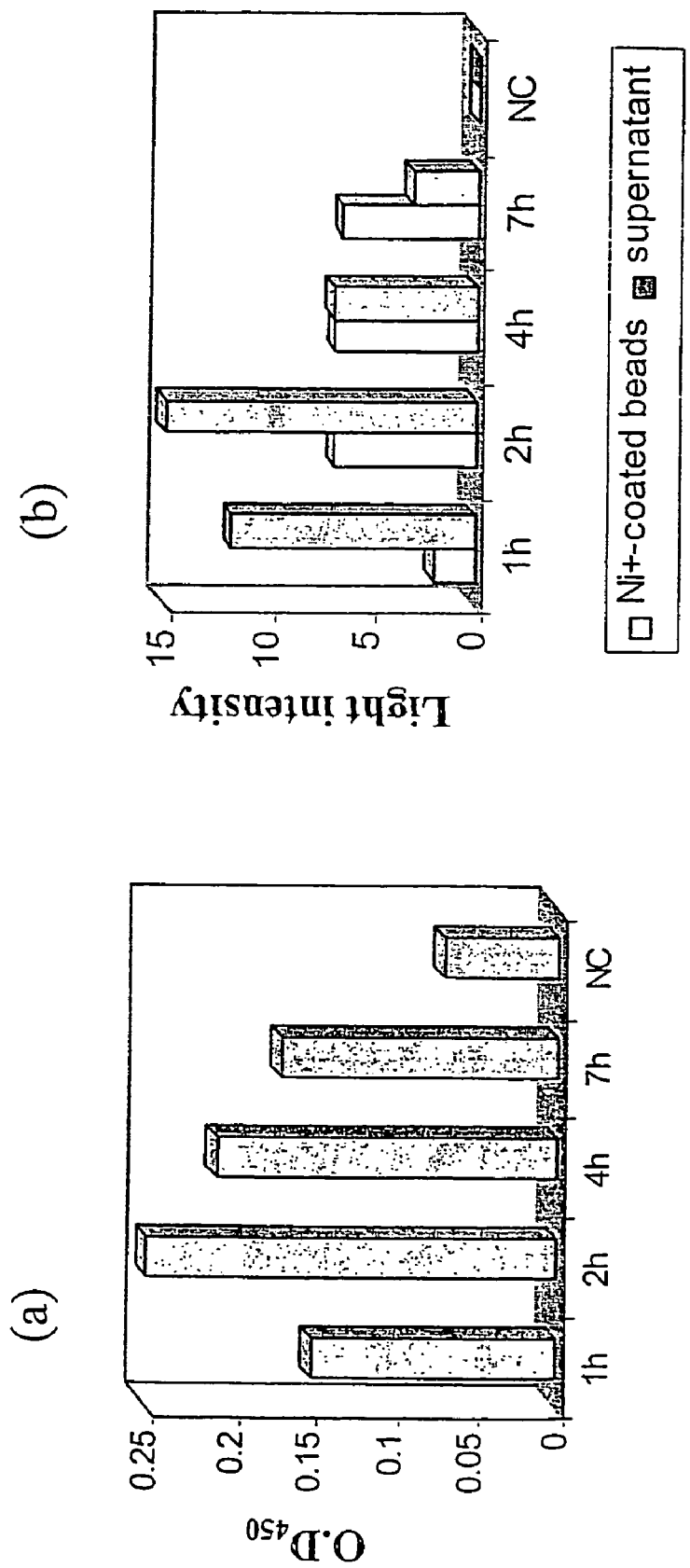

FIG. 13: Time-course of cell free protein synthesis by TNT and immobilisation in situ on Ni-NTA coated wells and magnetic beads.

Immobilisation of P5-17 human anti-progesterone $V_H$/K fragment onto Ni-NTA coated wells; assay by binding of biotinylated progesterone-BSA and streptavidin-HRP.

Immobilisation of luciferase on Ni-NTA coated beads; activity measured by luminometry.

Figure 14:
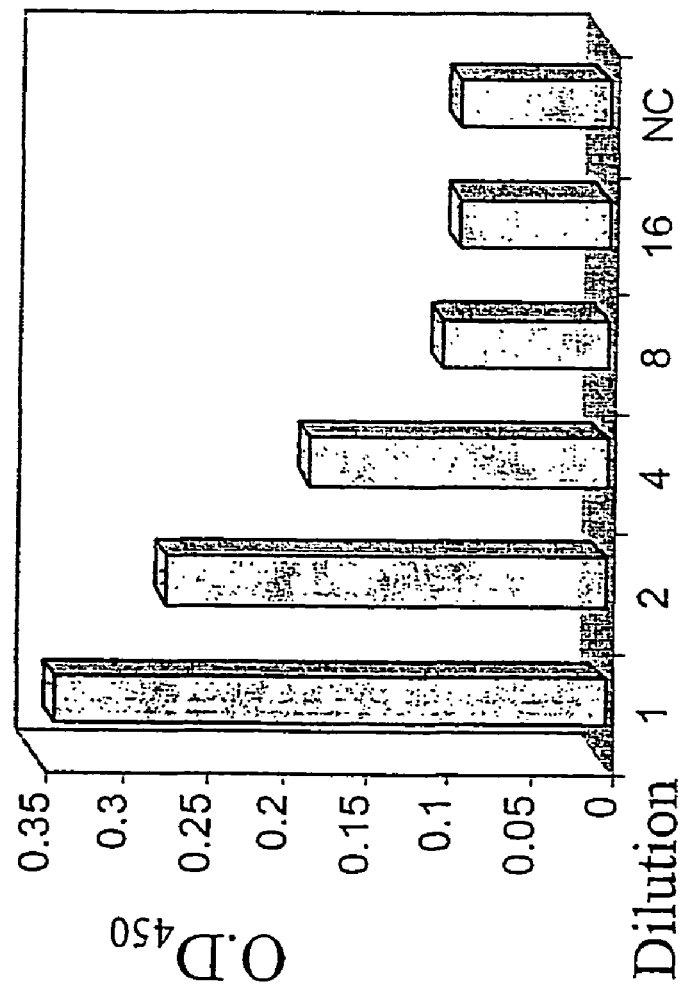

FIG. 14: P5-17 $V_H$/K immobilisation after cell free synthesis, serial dilution and transfer to Ni-NTA coated wells. $V_H$/K was detected by HRP linked anti-κ antibody.

Figure 15:
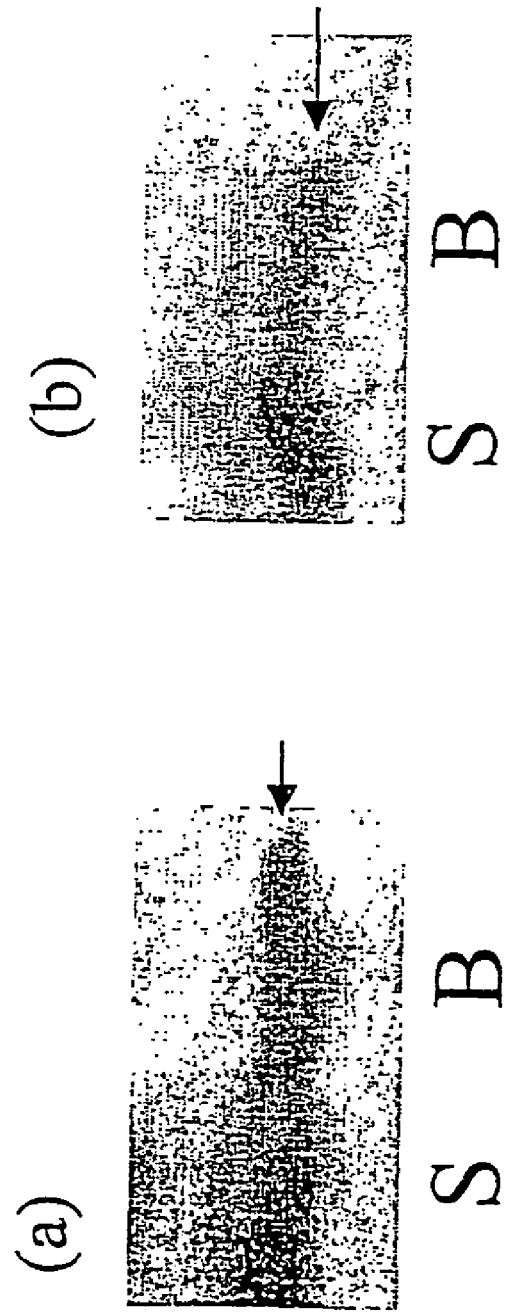

FIG. 15: Western blotting analysis of protein immobilised in situ onto Ni-NTA coated beads after cell free transcription/translation (PISA method).

S: free protein in supernatant after removal of beads; B: protein eluted from beads.

(a) P5-17 $V_H$/K (b) Luciferase

Figure 16:
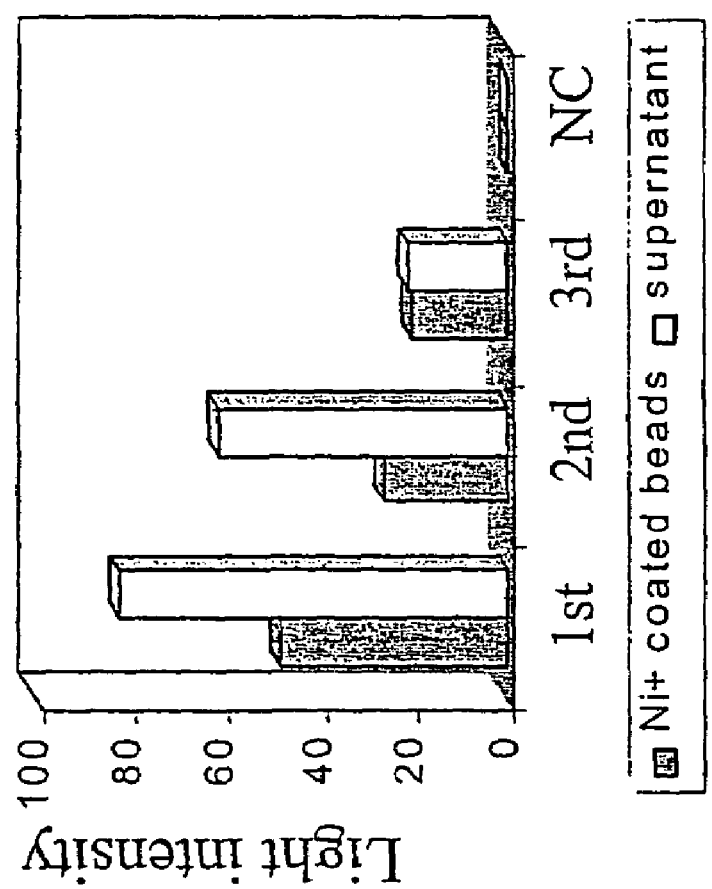

FIG. 16: Repeated assay of PISA-immobilised luciferase on beads.

PISA-immobilised luciferase on Ni-NTA coated magnetic beads was assayed by luminometry; the beads were washed after each use and stored at −20° C. for one week between $1^{st}$ and $2^{nd}$, and $2^{nd}$ and $3^{rd}$ assays. Supernatant was stored similarly.

Figure 17:
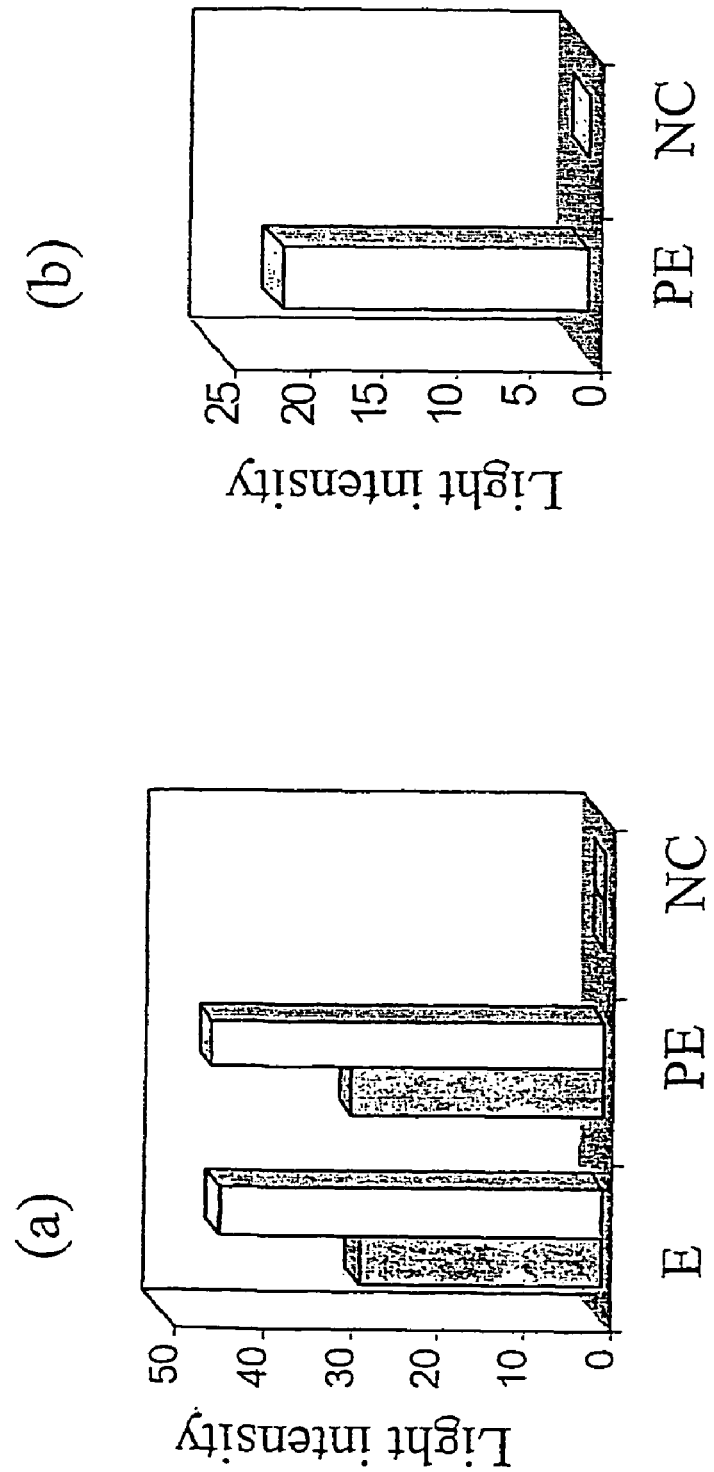

FIG. 17: Efficiency of consensus translation initiation sequence for both prokaryotic and eukaryotic expression.

(a) Expression in Coupled rabbit reticulocyte system (b) Expression in Coupled E. coli S30 system Luciferase expression was assayed by luminometry.

NC: cell free TNT mixture without DNA

E: DNA construct containing eukaryotic sequence alone

PE: DNA construct containing consensus sequence

Figure 18:
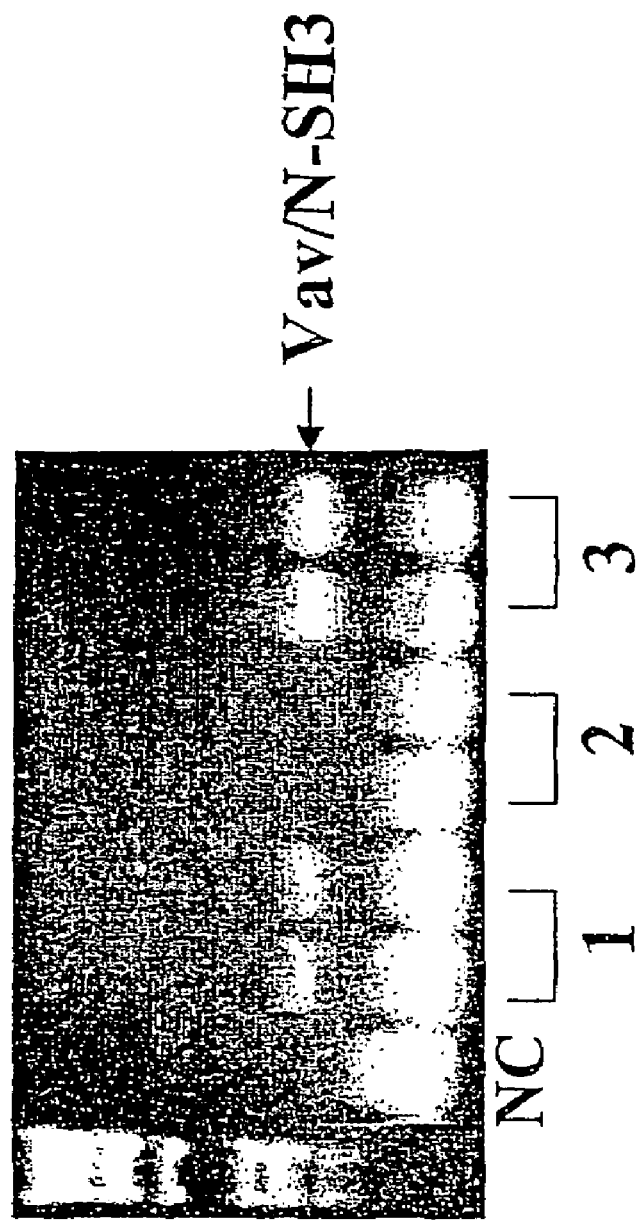

FIG. 18: Interaction of Vav/N-SH3 ribosome display complex with PISA-immobilised Grb2.

The marked tracks are

NC: Solution control for RT-PCR.

1. Vav/N-SH3 ribosome complexes interacted with Grb2 beads

2. Vav/SH2-C-SH3 ribosome complexes interacted with Grb2 beads

3. Ribosome complexes, expressed from a 1:1 mixture of Vav/N-SH3 and Vav/SH2-C-SH3 DNA, interacted with Grb2 beads FIG. 19: Interaction of ribosome display complex Grb2 with PISA-immobilised Vav/N-SH3.

The marked tracks are

1. Grb2 ribosome complexes interacted with Vav/SH2-C-SH3 beads

2. Grb2 ribosome complexes interacted with Vav/N-SH3 beads

Figure 20:
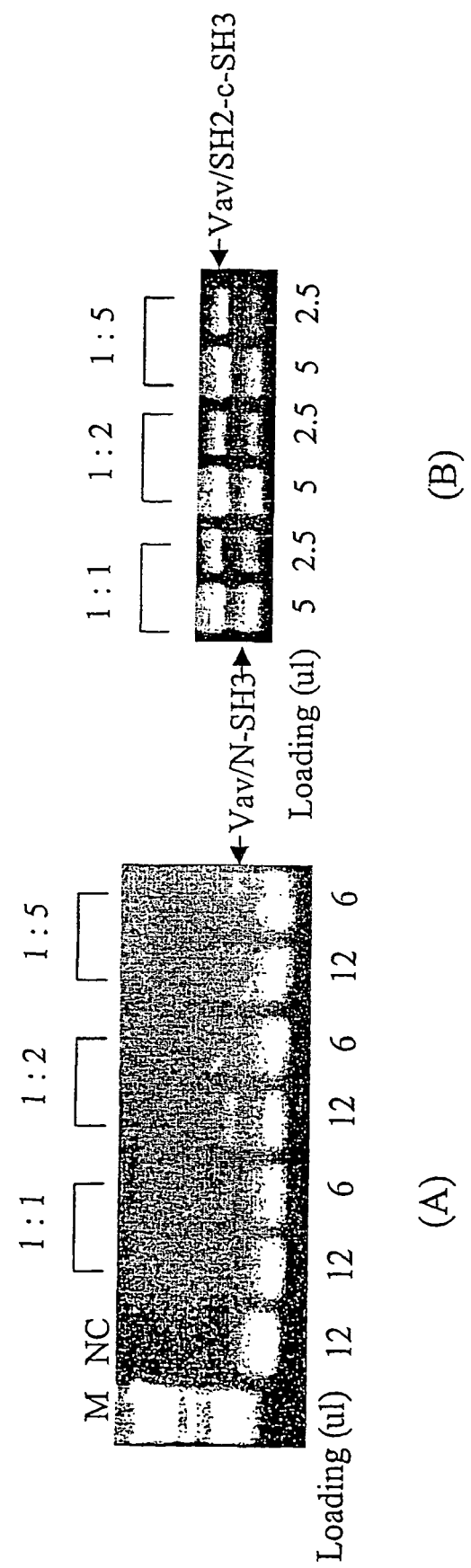

FIG. 20: Selection of protein-protein interaction from a library mixture.

The ribosome complex libraries were mixtures of Vav/N-SH3 and Vav/SH2-c-SH3 in the ratios 1:1, 1:2 and 1:5 as marked.

Gel (A): RT-PCR result after interaction of the mixtures with Grb2 beads

Gel (B): RT-PCR of starting mixtures

DESCRIPTION OF THE INVENTION

We describe a method for producing a protein array starting from DNA in which a number of native, functional proteins or domains are produced in parallel by in vitro synthesis using a cell free system for transcription and translation, followed by immobilisation of the products in a gridded format on a surface, using an isolation sequence tag incorporated into the proteins. In one embodiment, the array is formed in situ in a single step by performing protein expression in wells, on surfaces, or in the presence of beads, any of which are coated with immobilising molecules (affinity ligands) such as metal ions or antibodies.

Starting material can include genomic DNA, mRNA, cloned DNA fragments, or cDNA libraries, etc. The input DNA constructs for in vitro transcription/translation may be obtained by PCR (polymerase chain reaction) or RT (reverse transcription)-PCR amplification, using primers designed on any known DNA sequences, such as those from databases and genome projects. Alternatively, cloned plasmid DNA may be used. The cell free systems for protein synthesis are those such as rabbit reticulocyte, wheat germ, yeast or bacterial extracts. Numbers of individual native proteins or domains may be produced in parallel directly from the PCR DNA constructs. In one embodiment the reaction is carried out in the wells of multiwell plates. In another embodiment, proteins may be synthesised directly onto surfaces, such as glass, membranes or beads, for example by carrying out the reaction in microdroplets. The construct DNA may be added to the reaction volume or droplet or pre-immobilised to the surface. In the latter case, a DNA array is effectively created first and then used to create the protein array. The proteins can be adapted for rapid isolation, immobilisation or identification by inclusion of sequences such as hexahistidine or other peptide tags. If the wells or other surfaces in, or on, which the proteins are produced are precoated with an immobilising reagent such as nickel ions or anti-tag antibodies, the array will be formed as the proteins are produced in situ and reagent molecules can be removed by washing. The reaction may alternatively be performed in the presence of beads coated with an immobilising reagent, the beads being subsequently distributed in a gridded array format. Alternatively, the proteins can be transferred (e.g. by gridding robot) to secondary surfaces, such as plastic, glass, agarose, beads, nitrocellulose or other membranes.

Target molecules, such as labelled ligands, proteins or nucleic acids, may then be exposed to the array and binding to individual array locations detected by means of enzyme-coupled reaction, fluorescence, autoradiography or mass spectrometry. The arrays can thereby be used for screening of antibodies, ligands, protein interactions, etc. In some cases the arrayed proteins may be used in solution in order to perform biochemical studies. Retaining the gridded format, the solutions may also be transferred to filters or plates pre-coated with target molecules such as antigens, and binding detected by labelled secondary reagents.

The arrays can also be linked to library display systems. Thus, target molecules may be those of display libraries, such as phage or ribosome display libraries, in which the individual proteins are linked to encoding DNA or mRNA After binding to the array, interacting molecules are identified by amplification and identification of the linked DNA or mRNA, for example by cloning phage or by PCR, RT-PCR, hybridisation or other methods.

By utilising in vitro synthesis, the above methodology provides a rapid means of obtaining functional protein arrays directly from DNA, including proteins or domains known only from DNA sequence. It can replace cloning, in vivo expression systems and purification procedures. It avoids the problems of inclusion bodies, aggregation and degradation often encountered with bacterial expression. Since PCR and in vitro translation can be carried out using many samples simultaneously in parallel, such arrays will provide a high throughput capacity for analysis of protein expression, functional activity and interactions, making use in particular of the genetic information from genome projects.

Details of Method

DNA Constructs

The constructs for in vitro transcription/translation (FIG. 1) include: upstream T7 promoter and protein expression signals designed to allow genes to be expressed in either eukaryotic systems (FIG. 2a) or in both prokaryotic and eukaryotic systems (FIG. 2b); upstream or downstream sequences encoding a flexible linker (19 residues) and a tag sequence such as (his)6 [SEQ ID No. 1] or (his)6-SRAWRHPQFGG-(his)6 [SEQ ID No. 2] for protein immobilisation by metal affinity binding (FIG. 3) and/or a further peptide tag sequence for recognition by antibody or ligand; and a downstream translation stop codon. To create such constructs, the gene of interest is amplified separately by PCR or RT-PCR using specific primers derived from known DNA sequences, and the upstream and downstream elements are incorporated into the construct by PCR assembly.

For covalent immobilisation of constructs to a surface or bead, a DNA fragment encoding a transcription termination region is also included in the construct (FIG. 4). In addition, a chemical group for covalent linkage, such as a terminal amino group, can be introduced via modification of the 3' primer used in PCR The surface or bead is prepared for attachment by appropriate chemistry, such as DNA Immobiliser™ anthraquinone photo-coupling (Exiqon).

Design of PCR Construct for In Vitro Expression of Tagged Single Chain Antibodies FIG. 10 outlines a general PCR strategy for construction of DNA suitable for in vitro protein synthesis for PISA, using single chain antibody $V_H$/K fragments as example. The construct contains a T7 promoter for transcription by T7 RNA polymerase and Kozak sequence for translation initiation in cell free eukaryotic systems. To increase the efficiency of protein immobilisation on a Ni-NTA coated surface and allow the re-use of the protein arrays, a double $(His)_6$-tag domain was designed. A flexible 19 residue linker (Robinson and Sauer, 1998, Proc. Natl Acad. Sci. USA 95: 5929-5934) is placed between the protein to be arrayed and the His-tag domain, in order to reduce any possible interference of the tag sequence on folding of the attached protein. A poly$(A)_{28}$ tail and a transcription terminator are incorporated at the 3' end of the DNA to increase transcription efficiency. To ensure translation termination and release of the nascent polypeptide from the ribosome complex, two stop codons (TAATAA [SEQ ID No. 3]) are included following the double $(His)_6$-tag sequence.

A construct in which $V_H$/K fragments were linked to the double $(His)_6$tag domain ($V_H$/K-His) was produced by PCR with the following primers.

Primers for PCR Generation of $V_H$/K-Linker Fragments

T7Ab/back: 5'-GCA GC <u>TAATACGACTCACTATAGG</u>AACAGACCACCATG (C/G) AG GT(G/C) CA(G/C) CTC GAG (C/G)AG TCT GG-3' [SEQ ID No. 4]. This primer provides the T7 promoter and Kozak signal (underlined) and a degenerate sequence complementary to the 5' region of the antibody heavy chain (italics). The initiation codon is indicated in bold.

Ab-linker/for: 5'-<u>GCCACCGCCTCTAGAGCG</u> GCT CAG CGT CAG GGT GCT GCT-3' [SEQ ID No. 5]. This provides a sequence complementary to the 3' region of the human κ constant domain (Cκ) and a sequence (underlined) overlappping a linker-tag/back primer (see below) used for generation of the double $(His)_6$-tag domain.

Primers for PCR Generation of His-Tag Domain

Linker-tag/back: 5'-GCTCTAGAGGCGGTGGC TCT GGT GGC GGT TCT GGC GGT GGC ACC GGT GGC GGT TCT GGC GGT GGC AAA CGG GCT GAT GCT GCA [SEQ ID No. 6]. This provides a sequence (underlined) overlapping the Ab-linker/for primer used for $V_H$/K-linker constriction (above) and the linker sequence for PCR generation of the double $(His)_6$tag domain (below).

His-tag/for: 5'-TCC GGA TAT AGT TCC TCC-3' [SEQ ID No. 7].

Plasmid PTA-His Encoding a Double $(His)_6$-Tag Domain

The plasmid PTA-His contains a fragment encoding (in order) a flexible linker and a double $(His)_6$-tag, followed by two stop codons, a polyA tail and a transcription termination region. The sequence of this fragment was: GC TCT AGA ggc ggt ggc tct ggt ggc ggt tct ggc ggt ggc acc ggt ggc ggt tct ggc ggt ggc AAA CGG GCT GAT GCT GCA CATCACCATCACCATCACTCTAGAGCTTGGCGTCAC CCGCAGTTCGGTGGTCACCACCACCACCACCAC TAA TAA $(A)_{28}$ CCG CTG AGC AAT AACTAGCATAACCCCTTGGGGCCTCTAAACGGGTCT TGAGGGGTTTTTTG CTG AAA GGA GGA ACT ATA TCC GGA [SEQ ID No. 8]. Lower case sequence: linker encoding a 19 amino acid sequence; underlined sequence: double $(His)_6$ tag; bold: stop codons; $(A)_{28}$: poly A region which contains 28×A. Italics, underlined sequence: transcriptional terminator.

Construction of PCR Fragments

In general, standard PCR was carried out for 30 cycles to obtain the $V_H$/K-linker fragment and double $(His)_6$-tag domain in separate reactions using Taq polymerase (Qiagen, UK) according to the manufacturer's instructions. The resulting fragments were analysed and eluted from a 1% agarose gel using a gel extraction kit (Qiagen, ULK). For assembly, equal amounts (total 10-50 ng) of $V_H$/K-linker and double $(His)_6$tag domain were mixed and added to a PCR mixture containing 2.5 µl 10×PCR buffer (supplied with Taq DNA polymerase), 1 µl 2.5 mM dNTPs, 1 U Taq DNA polymerase and $H_2O$ to a final volume of 25 µl. After thermal cycling for 8 cycles (94° C. for 30 sec, 54° C. for 1 min and 72° C. for 1 min), 2 µl of the mixture was subjected to a second PCR in 50 µl for 30 cycles using primers T7Ab/back and His-tag/for to generate $V_H$/K-His (see FIG. 10).

In one embodiment the gridded format for transcription and translation comprises microwells of appropriate plates (e.g. 96, 384 or 1536 well polystyrene plates). Individual DNA constructs (1 µg) are dispensed into the wells, each containing a small volume (e.g. 1-50 µl) of cell free coupled transcription/translation systems such as the rabbit reticulocyte TNT T7 Quick for PCR DNA system (Promega), the TNT coupled wheat germ extract system (Promega) or E. coli S30 extract systems, together with methionine (0.02 mM). To label the protein, $^{35}S$ methionine or other labelled amino acids may be included. Plates are incubated for 1 hour at 30° C. Where the proteins contain immobilisation sequences, such as single or double hexahistidine tags or specific peptide tag sequence, they may be bound either by metal affinity on surfaces or beads coated with nickel or by antibody directed against the tag sequence. Therefore, if the wells in which the translation reaction occurs are precoated with Ni-NTA (nitrilotriacetic acid), such as HisSorb plates and strips (Qiagen), or anti-tag antibody, the proteins will be bound to the surface immediately after production to generate the array in situ. Similarly in the presence of beads coated with Ni-NTA the protein will become bound to the surface of the bead. The TNT reaction may also be carried out in noncoated wells and the translation mixture transferred, by manual or automated procedure, to another immobilising surface, such as glass coated with Ni-NTA, beads coated with Ni-NTA, or nitrocellulose or PVDF filter membranes. The unbound material is washed away leaving bound protein.

In alternative embodiments, the transcription/translation reactions are carried out on other surfaces, for example in droplets distributed on the surface of glass, membranes or agarose. The droplets may be oil-covered to prevent evaporation.

In embodiments where protein synthesis is carried out on immobilised DNA, the DNA constructs are first attached covalently or noncovalently to the surface, which may be a polystyrene microwell, modified glass, membrane, beads, agarose, or other surface, thus forming an immobilised DNA array on which protein synthesis can occur. The surface may also be coupled to immobilising reagents such as Ni-NTA or anti-tag antibody, in order to immobilise the protein as it is produced. The protein synthesis reaction is then performed in situ, for example in microwells or in microdroplets of the cell free system placed onto the DNA locations on glass, etc. Thus, in this embodiment, an immobilised DNA array is converted into a protein array via in vitro transcription/translation.

Array Quality Control

The presence of translated protein can be demonstrated using incorporated radiolabel or by antibody against a defined tag sequence shared by all the constructs. In this way the content of different wells or array locations can be normalised. Functionality may be demonstrated by specific ligand binding or enzyme activity, as appropriate to the protein.

EXAMPLES

Example 1

Creation of a Functional Protein Array Element by Simultaneous Expression and Immobilisation of an Antibody Fragment In Situ To demonstrate the creation of a functional protein array element in situ, a construct encoding a single-chain human anti-progesterone antibody $V_H$/K fragment (P5-17) was used (He et al., 1999, J. Immunol. Methods, 231:105). To prepare the construct for the protein array, the T7 promoter, expression signal and the double hexahistidine tag were incorporated into this fragment by PCR assembly. The PCR fragment (0.5 µgm) was mixed with 20 µl of coupled transcription/translation 'TNT for PCR DNA system' (Promega), total volume 25 µl, and the mixture was incubated at 30° C. for 1 hour on Ni-NTA coated wells of an 8-well HisSorb strip (Qiagen). As control, a non-antibody PCR fragment was used in the same transcription/translation and incubation conditions. After incubation, the strips were washed three times with PBS (phosphate buffered saline), 0.05% Tween. To demonstrate that the antibody fragment was expressed and immobilised on the surface of the wells, HRP (horseradish peroxidase)-anti-human κ antibody was applied. To test the binding activity of the immobilised P5-17, the wells were incubated with biotinylated progesterone-BSA (P-BSA) for 1 hour followed by detection with HRP-streptavidin for another hour. The HRP activity was developed and the colour read by ELISA reader at 450 nm.

The results of this two component array experiment show that the antibody fragment was successfully expressed in vitro, became bound in situ to the surface of the well (positive anti-κ binding) and was functional by the criterion of specific antigen binding FIG. 5). This result demonstrates that an individual protein array location can be constructed in a microwell by in vitro transcription and translation of PCR DNA and simultaneous immobilisation of the product to the surface of the well, with retained function of the protein.

Example 2

Figure 6:
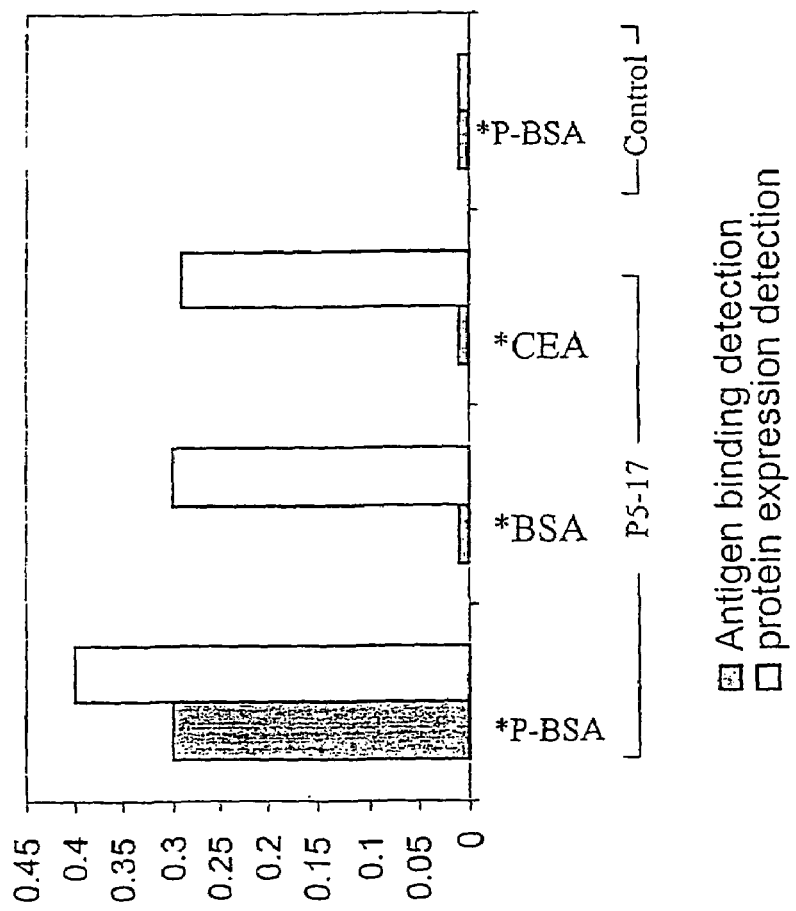

Creation of a Functional Protein Array Element by Expression In Vitro Followed by Immobilisation of an Antibody Fragment to a Separate Surface The P5-17 construct was transcribed and translated in microwells which were not coated with immobilising ligand, using the above conditions. After 1 hour, the well contents (translation mixture) were diluted 4-fold with PBS and 50 μl was transferred to Ni-NTAwells of HisSorb strips. After 1 hour, the wells were washed and exposed to biotinylated progesterone-BSA, BSA or CEA, followed after 1 hour by RP-streptavidin. FIG. 6 shows that the P5-17 protein was successfully produced and immobilised in the separate well, demonstrated by positive anti-κ binding, and that it was specific for progesterone-BSA. Thus a protein array element can be produced by in vitro transcription and translation of PCR-produced DNA and transfer of the product to the surface of an immobilising well, with retained function of the protein.

Example 3

Demonstration that Immobilisation Requires the Hexahistidine Tag

In order to rule out nonspecific protein localisation, a mouse antibody $V_H/K$ fragment of the anti-progesterone DB3 was produced as above using two different constructs. In one, the single hexahistidine tag sequence was included whereas in the other the sequence was deleted. Protein synthesis was carried out in HisSorb wells. Only the (His)6-containing construct was detected after translation by HRP-linked anti-mouse κ, implying that the immobilisation in situ requires the hexahistidine sequence.

Example 4

Functional Analysis of a Human Single Chain Anti-Progesterone $V_H/K$ (P5-17) by In Situ Protein Array A DNA construct encoding fragment P5-17 was generated by PCR The construct contains a T7 promoter and kozak sequence for in vitro protein synthesis, a double His-tag for protein immobilization and a polyA tail and transcription termination region for efficient protein production. Protein expression was carried out by adding the PCR construct to Promega 'TNT Quick for PCR' kit. The mixture was incubated on individual wells of a $Ni^+$-NTA coated plate (Qiagen) so that protein generation and in situ immobilisation proceeded simultaneously. Each well contained 25 μl of the TNT translation mixture and the mixture was incubated at 30° C. for 2-3 hrs with shaking. After washing with PBS-Tween (3 times), wells were treated with either biotinylated progesterone-BSA (P-BSA) or HRP-linked sheep anti-human-κ. For detection of biotinylated antigen, HRP-linked streptavidin was used. As controls, biotinylated BSA (BSA) and anti-mouse-κ (mouse) were used. FIG. 6 shows while biotinylated BSA produced no binding, the biotinylated progesterone-BSA was strongly bound (yellow colour). Similarly, the presence of P5-17 was only detected by anti-human-k (blue) and not by anti-mouse-κ. This experiment thus demonstrates the functional expression and immobilisation of P5-17 fragment in the 'protein in situ array' format (PISA).

Example 5

Quantitative Estimation of the Expression and In Situ Immobilisation of an Antibody Fragment by Western Blotting The antibody $V_H/K$ fragment produced as above was analysed by SDS-PAGE either before or after immobilisation on the microwell plate. To estimate the amount of fragment made, standard amounts of $V_H/K$ purified from E. coli were run alongside on the gel. FIG. 7 indicate that about 150 ng $V_H/K$ could be generated in 25 μl TNT mixture. After in situ immobilisation, about 50% of the total $V_H/K$ remained in the supernatant and 30% was eluted from the plate in this case, indicating a binding of about 50 ng.

Example 6

Screening of Cloned Antibody $V_H/K$ Fragments from a Library by a Functional Protein In Situ Array (PISA)

The array was established by the protein in situ array procedure using PCR products from individual E. coli clones carrying DNA encoding human anti-progesterone $V_H/K$ fragments. The clones were obtained by E. coli transformation with a transgenic mouse $V_H/K$ library either before or after progesterone-BSA selection (He et al. 1999, J. Immunological Methods 231: 105). In FIG. 8, the array elements were displayed in duplicate, with pre-selection clones numbered 1-5 (top) and post selection clones labelled P5-8, 10, 16, 17. The array was developed with either biotinylated progesterone-BSA followed by HRP-linked streptavidin (left) or ERP linked sheep anti-human κ (right). The array shows that the 4 clones after antigen selection were positive for antigen binding whereas those before selection were negative, a result confirmed independently by E. coli expression. The anti-κ detection showed that the $V_H/K$ fragments were expressed and immobilised for all clones.

Example 7

Coupled Expression and Immobilisation of Luciferase on Magnetic Beads

Luciferase was chosen for generation of a functional enzyme immobilised on the solid surface of magnetic beads using the PISA procedure. A construct encoding luciferase with the C-terminal double His-tag (Luci-His) was produced by PCR as described for $V_H/K$; as a control, luciferase DNA lacking the His-tag domain (Luci) was also PCR generated. Primers for PCR generation of luciferase DNA were as follows:

T7 Luci/back: GCA GC<u>TAATACGACTCACTATAGG</u>AACAGACCACCATG GAA GAC GCC AAA AAC [SEQ ID No. 9]. The T7 promoter and Kozak signal are underlined. Italics indicate the sequence complementary to the 5' region of luciferase. ATG is the initiation codon.

Luci-linker/for: <u>GCCACCGCCTCTAGAGCG</u> CAA TTT GGA CTT TCC GCC [SEQ ID No. 10]. The underlined sequence overlaps a linker-tag/back, primer (see above) used for generation of the double (His)$_6$-tag domain.

After cell free expression in the presence of Ni-NTA coated magnetic beads, the latter were separated from the translation mixture and washed. Luciferase activity free in the translation mixture supernatant and immobilised on the beads was measured using a luminometer (FIG. 11). While the luciferase construct lacking the His-tag domain only produced activity in the translation mixture, Luci-His generated activity both in the mixture and on the beads, demonstrating the successful immobilisation of functional luciferase through the double-His tag domain.

Example 8

Generation of Protein In Situ Array (PISA) Elements from Immobilised DNA

In this example, PCR DNA was immobilised on magnetic beads and used as template to generate His-tagged proteins which became immobilised in situ on the surface of Ni-NTA coupled wells or magnetic agarose beads.

PCR DNA fragments encoding the human anti-progesterone $V_H$/K fragment P5-17 or luciferase was biotinylated using a 3' primer labelled with biotin. Coupling to beads was achieved by mixing the biotinylated PCR fragment with streptavidin-linked magnetic beads (Promega) and incubating at room temperature for 30 min with gentle rotation. The DNA-coupled beads were collected and washed three times with 0.5 ml phosphate buffered saline (PBS).

To create an array element of P5-17 $V_H$/K by PISA on a Ni-NTA coated well surface, 25 µl of TNT mixture containing 0.02 mM methionine and 0.5 mM Mg acetate was mixed with P5-17 DNA-coupled beads (above) and the mixture added into the well of a Ni-NTA coated plate (Ni-NTA HisSorb strips, Qiagen). After incubation for 2 hrs with shaking, the plate was washed 100 µl wash buffer (50 mM NaH$_2$PO$_4$, 300 mM NaCl, 20 mM imidazole, pH 8.0), followed by a final wash with 100 µl phosphate-buffered saline (PBS). The wells were probed with either biotinylated progesterone-BSA or HRP-linked anti-human κ chain. TNT mixture without PCR-coated beads was used as control. FIG. 12(a) shows while the negative control (TNT mixture without DNA-coupled beads) had no detected binding activity, wells incubated with P5-17 DNA-coupled beads generated positive signals using either the antigen, biotinylated progesterone-BSA, and HRP-linked streptavidin, or HRP-linked anti-human κ chain.

To create an array element of luciferase by PISA on the surface of Ni-NTA-coated agarose beads, 25 µl of TNT mixture containing 0.02 mM methionine and 0.5 mM Mg acetate was added to a mixture of luciferase DNA-coupled beads and Ni-NTA coated beads (Qiagen). The mixture was incubated at 30° C. for 2 hr with gentle shaking. The beads were washed as above and luciferase activity measured by luminometry. A TNT mixture containing luciferase DNA-coated beads, but without Ni-NTA coated beads, was used as control. FIG. 12(b) shows that both supernatant and beads from the TNT reaction mixture containing DNA-coupled and Ni-NTA coated beads generated luciferase activity, whereas with the control mixture lacking Ni-NTA beads, enzyme activity was only detected in the supernatant.

These experiments demonstrate the potential to generate immobilised protein from immobilised DNA by in vitro synthesis (PISA method). This could be used to convert a DNA array into a protein array.

Example 9

Time-Course for Creating a Protein In Situ Array (PISA) on Ni-NTA Wells and Magnetic Beads To measure the optimal time for immobilisation of in vitro synthesised protein onto Ni-NTA coated wells, 100 µl of TNT mixture containing P5-17 $V_H$/K DNA was subdivided into 25 µl aliquots and added to four Ni-NTA coated wells. The mixtures were incubated at 30° C. for 1, 2, 4 and 7 hours respectively. After washes, HRP-linked anti-human κ was used to detect the immobilised P5-17 antibody fragment (FIG. 13a). Two hours incubation produced the highest level of $V_H$/K immobilisation.

To measure the optimal time for immobilisation of in vitro synthesised protein onto Ni-NTA linked magnetic beads, 100 µl of TNT mixture containing luciferase DNA was subdivided into 25 µl aliquots and added to Ni-NTA coated beads. The mixtures were incubated at 30° C. for 1, 2, 4 and 7 hours. After washes, luciferase activity was measured by luminometry (FIG. 13b). This revealed that while both free and immobilised luciferase activity reached a peak in activity in 2 hr, free luciferase declined significantly after 2 hours.

Example 10

Immobilisation of His-Tagged P5-17 $V_H$/K After Cell Free Synthesis and Transfer to Ni-NTA Coated Wells with Serial Dilution The His-tagged P5-17 $V_H$/K fragment was expressed in 50 µl rabbit reticulocyte lysate. After serial two-fold dilution, 25 µl was added in duplicate to individual Ni-NTA coated wells. After 2 h incubation at 30° C., wells were washed and P5-17 immobilisation was detected using HRP-linked anti-human κ chain (FIG. 14). The result shows that $V_H$/K was detectable on the well surface after up to 4 fold dilution.

Example 11

Analysis of Protein Immobilisation onto Ni-NTA Coated Beads by Western Blotting

Western blotting was applied to estimate the efficiency of protein immobilisation onto Ni-NTA coated beads. Both P5-17 human anti-progesterone $V_H$/K and luciferase were immobilised onto Ni-NTA coated beads using the PISA procedure. The beads were then boiled in SDS sample buffer before running on PAGE, in parallel with supernatant protein remaining in the TNT mixture after removal of beads. After Western blotting, transferred protein was detected with HRP-linked anti-(His)$_6$ antibody and quantified by densitometry. The results show that 40-50% of the translated protein was eluted from Ni-NTA coated beads (FIG. 15, arrowed) (cf. similar result using Ni-NTA coated wells, example 5).

Example 12

Re-Use of Luciferase-Immobilised Beads after Storage

To test if arrayed protein immobilised by the PISA procedure can be re-assayed, luciferase-immobilised beads were generated as in example 7 and luciferase activity from both free in the supernatant and immobilised on the beads was analysed in parallel. After the first measurement, the beads were washed three times with washing buffer and twice with PBS; they were resuspended in 50 µl PBS and stored at −20° C. for one week. The supernatant was also stored at −20° C. for the same period. The second and third measurements of luciferase activity including washing and storage of the samples were performed as for the first. FIG. 16 shows that PISA-immobilised luciferase could be reassayed twice with positive results.

Example 13

Efficiency of Consensus Sequence for Both Prokaryotic and Eukaryotic Expression The designed PISA construct includes a novel consensus sequence for protein translation initiation in both prokaryotic and eukaryotic systems (FIG. 2). In order to validate its effectiveness, a luciferase construct containing the consensus initiation sequence was tested for protein expression in both coupled rabbit reticulocyte lysate and coupled E. coli S30 systems. FIG. 17 shows that the sequence allowed production of functional luciferase in both systems. A comparison also showed that it generated luciferase as efficiently as the regular sequence for eukaryotic systems (FIG. 17a).

E: eukaryotic initiation sequence alone.

PE: combined prokaryotic and eukaryotic initiation sequences (novel)

Example 14

Demonstration of Protein-Protein Interactions by Combination of Ribosome Display and PISA: Interaction of Grb2 with Vav/N-SH3

Interaction of the signalling proteins Vav and Grb2 (Ye and Baltimore (1994) PNAS 91:12629-12633) was chosen as a model with which to demonstrate protein-protein interaction through a combination of ribosome display and PISA protein arrays. In intact mammalian haematopoietic cells, Vav binds to the adaptor molecule Grb2 to initiate signal transduction via Ras activation. Vav contains Src homology 2 and 3 domains (SH2, SH3), in the order (N-SH3)-SH2-(C-SH3). Interaction with Grb2 was first identified by yeast two-hybrid screen and subsequently shown by filter binding assay to involve a highly specific binding between the N-SH3 domain of Vav and the C-SH3 domain of Grb2 (Ye and Baltimore, 1994). The Grb2 C-SH3 domain bound the N-SH3 domain of Vav, but not the Vav/SH2-(C-SH3) domains. Ye and Baltimore also prepared GST-Grb2 coupled to glutathione-conjugated agarose beads in order to detect interaction with Vav and showed that full-length Grb2 on beads precipitated full length Vav from cell lysates.

We generated DNA for the Vav/N-SH3 fragment (comprising the N-terminal SH3 domain), Vav/SH2-C-SH3 (comprising the SH2 domain and linked C-terminal SH3 domain), and full length Grb2 by PCR, from plasmids provided by Dr Martin Turner (Babraham Institute), using primers based on their corresponding DNA sequence. In the constructs for ribosome display, a human Cκ domain was assembled at the C-terminus of the protein, while in the constructs for protein array (PISA) format the double $(His)_6$ domain was added to the C-terminus (no Cκ domain).

(a) Interaction of Vav/N-SH3 Ribosome Display Complex with PISA-Generated Grb2

Ribosome display for Vav/N-SH3 and Vav/SH2-C-SH3 proteins was by the eukaryotic method (He and Taussig (1997) Nucl. Acids Res. 25:5132). PISA-immobilised, full length Grb2 was generated on Ni-NTA coated beads by cell free synthesis as described herein. Grb2 beads were mixed with ribosome displayed Vav/N-SH3, Vav/SH2-C-SH3 or a 1:1 mixture of Vav/N-SH3:Vav/SH2-C-SH3, respectively. The interactions were carried out on ice for 2 hr and the ribosome complexes interacting with Grb2 beads were isolated by a magnetic concentrator. After washing the beads three times with 50 µl washing buffer (PBS, 0.1% BSA, 0.05% Tween, 5 mM Mg acetate) followed by two washes with water, the beads were subjected to RT-PCR using universal primers for both Vav/N-SH3 and Vav/SH2-C-SH3 constructs (T7A1 and evol 4). FIG. 18 shows that while DNA encoding Vav/SH2-C-SH3 was not detected, Vav/N-SH3 was efficiently recovered from both Vav/N-SH3 and the 1:1 mixture, a result consistent with the reported interaction between Grb2 and Vav/N-SH3.

(b) Interaction of Grb2 Ribosome Display Complex with PISA-Generated Vav/N-SH3

Figure 19:
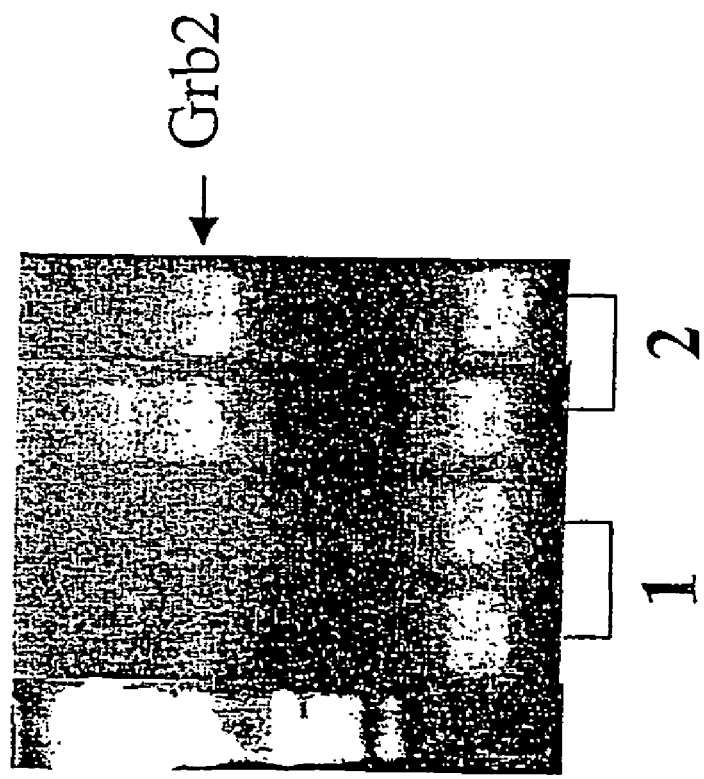

To confirm the interaction observed above, the displayed format of the proteins was reversed, i.e Vav/N-SH3 and Vav/SH2-C-SH3 were expressed as PISA-immobilised proteins on magnetic beads and Grb2 was in the form of a ribosome display complex. The conditions for interaction and washing were as above. FIG. 19 shows that RT-PCR recovery of Grb2 DNA was much stronger from Vav/N-SH3 beads than from Vav/SH2-C-SH3 beads. This again confirms a specific interaction between Grb2 and Vav/N-SH3.

(c) Selection of Interacting Molecules from a Ribosome Display Library

To test if interacting molecules could be selected from a ribosome display library, mixtures of ribosome complexes comprising Vav/N-SH3 and Vav/SH2-C-SH3 in 1:1, 1:2 and 1:5 ratios were produced and reacted with PISA-generated Grb2 beads. Conditions for interaction followed by washes were as in (a) above. DNA encoding the selected interacting molecules was recovered by RT-PCR As a comparison, the unselected ribosome display libraries were also subjected to RT-PCR using the same primers as in DNA recovery. FIG. 20 shows while both Vav/N-SH3 and Vav/SH2-c-SH3 were amplified proportionally by RT-PCR from the original libraries, only Vav/N-SH3 was demonstrably recovered after interaction of library mixtures of different ratios with Gib2-linked beads, demonstrating selection of the interacting molecule Vav/N-SH3.

These experiments demonstrate that the combined use of ribosome display and PISA can detect protein-protein interactions and allows recovery and identification of DNA for the interacting partners. It will be possible thereby to screen ribosome display libraries against PISA protein arrays for discovery of novel interactions.

The invention claimed is:

1. An in situ method for producing an immobilized protein, domain or peptide array using wells of plates and a cell free system, wherein the method comprises the steps of:
   (a) providing DNA constructs that comprise (i) DNA sequences that encode proteins, domains or peptides, and (ii) DNA sequences that allow transcription and translation of the DNA sequences of (i) in a cell free system, wherein the encoded proteins, domains or peptides can be covalently or non-covalently attached to the wells of the plates;
   (b) distributing the DNA constructs in a gridded format into the wells of the plates that carry a ligand or reagent for immobilization of the proteins, domains or peptides encoded by the DNA sequences of (i); and
   (c) allowing transcribing and translating the DNA constructs of (b) to provide proteins, domains or peptides, in the gridded format, using the cell free system such that the translated protein products, domain products or peptide products are immobilized during production to the same wells in which the transcription and translation took place, thereby creating the protein, domain or peptide array.

2. An in situ method producing an immobilized protein, domain or peptide array using surfaces of substrates and a cell free system, wherein the method comprises the steps of:
   (a) providing DNA constructs that comprise (i) DNA sequences that encode proteins, domains or peptides, and (ii) DNA sequences that allow transcription and translation of the DNA sequences of (i) in a cell free system, wherein the encoded proteins, domains or peptides can be covalently or non-covalently attached to the surfaces of substrates;
   (b) distributing the DNA constructs in a gridded format onto the surfaces of the substrates that carry a ligand or reagent for immobilization of the proteins, domains or peptides encoded by the DNA sequences of (i); and
   (c) transcribing and translating the DNA constructs of (b) to provide proteins, domains or peptides, in the gridded format, using the cell free system such that the translated protein products, domain products or peptide products are immobilized during production to the same surfaces which were present when the transcription and translation took place, thereby creating the protein, domain or peptide array.

3. The method according to claim 1, wherein the DNA constructs are first transcribed into mRNA and the mRNA is then translated in a separate reaction.

4. The method according to claim 1, wherein the cell free system allows coupled transcription and translation of DNA, or allows separate transcription of DNA and translation of mRNA, and wherein the cell free system is of rabbit reticulocyte, wheat germ, yeast, bacterial or other eukaryotic or prokaryotic origin.

5. The method according to claim 2, wherein the DNA constructs are first transcribed into mRNA and the mRNA is then translated in a separate reaction.

6. The method according to claim 2, wherein the cell free system allows coupled transcription and translation of DNA, or allows separate transcription of DNA and translation of mRNA, and wherein the cell free system is of rabbit reticulocyte, wheat germ, yeast, bacterial or other eukaryotic or prokaryotic origin.

7. An in situ method for immobilizing proteins, domain or peptide using beads and a cell free system for use in an array having a gridded format, wherein the method comprises the steps of:
   (a) providing DNA constructs that comprise (i) DNA sequences that encode proteins, domains or peptides, and (ii) DNA sequences that allow transcription and translation of the DNA sequences of (i) in a cell free system, wherein the encoded proteins, domains or peptides can be covalently or non-covalently attached to the beads;
   (b) distributing the DNA constructs in the gridded format in the presence of the beads that carry a ligand or reagent for immobilization of the proteins, domains or peptides encoded by the DNA sequences of (i); and
   (c) allowing transcribing and translating the DNA constructs of (b) to provide proteins, domains or peptides, using the cell free system such that the translated protein products, domain products or peptide products are immobilized during production to the same beads which were present when the transcription and translation took place, thereby creating the protein, domain or peptide array.

8. The method according to claim 7, wherein the DNA constructs are first transcribed into mRNA and the mRNA is then translated in a separate reaction.

9. The method according to claim 7, wherein the cell free system allows coupled transcription and translation of DNA, or allows separate transcription of DNA and translation of mRNA, and wherein the cell free system is of rabbit reticulocyte, wheat germ, yeast, bacterial or other eukaryotic or prokaryotic origin.

10. The method according to claim 1, in which the array is a functional protein, domain or peptide array.

11. The method according to claim 2, in which the array is a functional protein, domain or peptide array.

12. The method according to claim 7, in which the array is a functional protein, domain or peptide array.

* * * * *

UNITED STATES PATENT AND TRADEMARK OFFICE
CERTIFICATE OF CORRECTION

| | |
|---|---|
| PATENT NO. | : 7,674,752 B2 |
| APPLICATION NO. | : 10/344607 |
| DATED | : March 9, 2010 |
| INVENTOR(S) | : Mingyue He et al. |

Page 1 of 1

It is certified that error appears in the above-identified patent and that said Letters Patent is hereby corrected as shown below:

On Title page, Item (73), under Assignee, please delete "Discema Limited" and insert -- Discerna Limited --.

Signed and Sealed this

Eighth Day of June, 2010

David J. Kappos
*Director of the United States Patent and Trademark Office*